(12) United States Patent
Zucherman et al.

(10) Patent No.: US 7,503,935 B2
(45) Date of Patent: *Mar. 17, 2009

(54) METHOD OF LATERALLY INSERTING AN ARTIFICIAL VERTEBRAL DISK REPLACEMENT WITH TRANSLATING PIVOT POINT

(75) Inventors: James F. Zucherman, San Francisco, CA (US); Ken Y. Hsu, San Francisco, CA (US); Charles J. Winslow, Walnut Creek, CA (US); Scott A. Yerby, Montara, CA (US); Steven T. Mitchell, Pleasant Hill, CA (US); John J. Flynn, Concord, CA (US)

(73) Assignee: Kyphon SARL (CH)

( * ) Notice: Subject to any disclaimer, the term of this patent is extended or adjusted under 35 U.S.C. 154(b) by 437 days.

This patent is subject to a terminal disclaimer.

(21) Appl. No.: 10/981,807

(22) Filed: Nov. 5, 2004

(65) Prior Publication Data
US 2005/0143820 A1 Jun. 30, 2005

Related U.S. Application Data

(60) Provisional application No. 60/526,724, filed on Dec. 2, 2003.

(51) Int. Cl.
*A61F 2/44* (2006.01)
(52) U.S. Cl. .................. 623/17.15; 623/17.11
(58) Field of Classification Search ... 623/17.11–17.16; 606/246, 247, 60
See application file for complete search history.

(56) References Cited

U.S. PATENT DOCUMENTS

| | | | |
|---|---|---|---|
| 2,456,806 | A | 12/1948 | Wolffe |
| 2,677,369 | A | 5/1954 | Knowles |
| 3,426,364 | A | 2/1969 | Lumb |
| 3,867,728 | A | 2/1975 | Stubstad et al. |
| 3,875,595 | A | 4/1975 | Froning |
| 4,309,777 | A | 1/1982 | Patil |
| 4,349,921 | A | 9/1982 | Kuntz |
| 4,369,769 | A | 1/1983 | Edwards |
| 4,401,112 | A | 8/1983 | Rezaian |
| 4,479,491 | A | 10/1984 | Martin |
| 4,501,269 | A | 2/1985 | Bagby |

(Continued)

FOREIGN PATENT DOCUMENTS

CA        2015507        1/1991

(Continued)

OTHER PUBLICATIONS

International Search Report for PCT/US06/10521 (mailed Nov. 22, 2006).

(Continued)

*Primary Examiner*—Alvin J Stewart
(74) *Attorney, Agent, or Firm*—Haynes and Boone, LLP

(57) ABSTRACT

An implant that can be placed between two vertebrae using a lateral insertion method is described. The implant is characterized by having a first end plate and a second end plate with a hemi-cylindrical spacer extending from the second end plate. The hemi-cylindrical spacer fits within a socket on the first end plate and allows for pivotal or rotational motion and also for twisting motion.

22 Claims, 24 Drawing Sheets

U.S. PATENT DOCUMENTS

| | | |
|---|---|---|
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,636,217 A | 1/1987 | Ogilvie |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Büettner-Janz et al. |
| 4,759,769 A | 7/1988 | Hedman et al. |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,878,915 A | 11/1989 | Brantigan |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Fuhrmann et al. |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A | 1/1993 | Aust et al. |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,352,225 A | 10/1994 | Yuan et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,390,683 A | 2/1995 | Pisharodi |
| 5,395,317 A | 3/1995 | Kambin |
| 5,395,372 A | 3/1995 | Holt et al. |
| 5,397,364 A * | 3/1995 | Kozak et al. ............. 623/17.11 |
| 5,401,269 A * | 3/1995 | Buttner-Janz et al. .... 623/17.15 |
| 5,415,704 A | 5/1995 | Davidson |
| 5,423,816 A | 6/1995 | Lin |
| 5,423,817 A | 6/1995 | Lin |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,454,812 A | 10/1995 | Lin |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,507,816 A | 4/1996 | Bullivant |
| 5,514,180 A | 5/1996 | Heggeness et al. |
| 5,522,899 A | 6/1996 | Michelson |
| 5,527,312 A | 6/1996 | Ray |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A | 9/1996 | Büttner-Janz |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,603,713 A | 2/1997 | Aust .......................... 606/61 |
| 5,609,634 A | 3/1997 | Voydeville |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |
| 5,645,598 A | 7/1997 | Brosnahan, III |
| 5,645,599 A | 7/1997 | Samani |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |

| Patent | Date | Inventor |
|---|---|---|
| 5,683,464 A | 11/1997 | Wagner et al. |
| 5,683,465 A | 11/1997 | Shinn et al. |
| 5,693,100 A | 12/1997 | Pisharodi |
| 5,697,889 A | 12/1997 | Slotman et al. |
| 5,697,977 A | 12/1997 | Pisharodi |
| 5,700,292 A | 12/1997 | Margulies |
| 5,702,449 A | 12/1997 | McKay |
| 5,702,450 A | 12/1997 | Bisserie |
| 5,702,454 A | 12/1997 | Baumgartner |
| 5,702,455 A | 12/1997 | Saggar |
| 5,716,415 A | 2/1998 | Steffee |
| 5,716,416 A | 2/1998 | Lin |
| 5,741,253 A | 4/1998 | Michelson |
| 5,755,732 A | 5/1998 | Green et al. |
| 5,755,796 A | 5/1998 | Ibo et al. |
| 5,755,798 A | 5/1998 | Papavero et al. |
| 5,766,252 A | 6/1998 | Henry et al. |
| 5,772,661 A | 6/1998 | Michelson |
| 5,776,196 A | 7/1998 | Matsuzaki et al. |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,797,909 A | 8/1998 | Michelson |
| 5,800,438 A | 9/1998 | Tuke et al. |
| 5,800,550 A | 9/1998 | Sertich |
| 5,824,093 A | 10/1998 | Ray et al. |
| 5,824,094 A | 10/1998 | Serhan et al. |
| 5,827,328 A | 10/1998 | Buttermann |
| 5,836,948 A | 11/1998 | Zucherman et al. |
| 5,860,973 A | 1/1999 | Michelson |
| 5,860,977 A | 1/1999 | Zucherman et al. |
| 5,865,845 A | 2/1999 | Thalgott |
| 5,865,846 A | 2/1999 | Bryan et al. |
| 5,876,404 A | 3/1999 | Zucherman et al. |
| 5,885,292 A | 3/1999 | Moskovitz et al. |
| 5,885,299 A | 3/1999 | Winslow et al. |
| 5,888,222 A | 3/1999 | Coates et al. |
| 5,888,224 A | 3/1999 | Beckers et al. |
| 5,888,226 A | 3/1999 | Rogozinski |
| 5,888,227 A | 3/1999 | Cottle .................. 623/17 |
| 5,891,147 A | 4/1999 | Moskovitz et al. |
| 5,893,889 A | 4/1999 | Harrington |
| 5,893,890 A | 4/1999 | Pisharodi |
| 5,895,426 A | 4/1999 | Scarborough et al. |
| 5,895,427 A | 4/1999 | Kuslich et al. |
| 5,895,428 A | 4/1999 | Berry |
| 5,899,941 A | 5/1999 | Nishijima et al. |
| 5,906,616 A | 5/1999 | Pavlov et al. |
| 5,919,235 A | 7/1999 | Husson et al. |
| 5,928,284 A | 7/1999 | Mehdizadeh |
| 5,944,754 A | 8/1999 | Vacanti |
| 5,945,115 A | 8/1999 | Dunn et al. |
| 5,961,554 A | 10/1999 | Jamson et al. |
| 5,964,807 A | 10/1999 | Gan et al. |
| 5,976,186 A | 11/1999 | Bao et al. |
| 5,980,572 A | 11/1999 | Kim et al. |
| 5,984,967 A | 11/1999 | Zdeblick et al. |
| 5,989,291 A | 11/1999 | Ralph et al. |
| 6,001,130 A | 12/1999 | Bryan et al. |
| 6,004,573 A | 12/1999 | Rathi et al. |
| 6,005,162 A | 12/1999 | Constantz |
| 6,019,792 A | 2/2000 | Cauthen |
| 6,019,793 A | 2/2000 | Perren et al. |
| 6,022,376 A | 2/2000 | Assell et al. |
| 6,039,761 A | 3/2000 | Li et al. |
| 6,039,763 A | 3/2000 | Shelokov |
| 6,042,582 A | 3/2000 | Ray |
| 6,045,579 A | 4/2000 | Hochshuler et al. |
| 6,045,580 A | 4/2000 | Scarborough et al. |
| 6,048,342 A | 4/2000 | Zucherman |
| 6,051,648 A | 4/2000 | Rhee et al. |
| 6,068,630 A | 5/2000 | Zucherman |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochshuler et al. |
| 6,086,613 A | 7/2000 | Camino et al. |
| 6,090,112 A | 7/2000 | Zucherman et al. |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,110,210 A | 8/2000 | Norton et al. |
| 6,111,164 A | 8/2000 | Rainey et al. |
| 6,113,637 A | 9/2000 | Gill et al. |
| 6,113,638 A | 9/2000 | Williams et al. |
| 6,113,639 A | 9/2000 | Ray et al. |
| 6,120,502 A | 9/2000 | Michelson |
| 6,120,503 A | 9/2000 | Michelson |
| 6,123,705 A | 9/2000 | Michelson |
| 6,126,689 A | 10/2000 | Brett |
| 6,127,597 A | 10/2000 | Beyar et al. |
| 6,129,763 A | 10/2000 | Chauvin et al. |
| 6,132,430 A | 10/2000 | Wagner |
| 6,132,465 A | 10/2000 | Ray et al. |
| 6,136,001 A | 10/2000 | Michelson |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,149,650 A | 11/2000 | Michelson |
| 6,149,652 A | 11/2000 | Zucherman et al. |
| 6,149,686 A | 11/2000 | Kuslich et al. |
| 6,152,926 A | 11/2000 | Zucherman et al. |
| 6,156,038 A | 12/2000 | Zucherman et al. |
| 6,156,067 A | 12/2000 | Bryan et al. |
| 6,159,215 A | 12/2000 | Urbahns et al. |
| 6,162,252 A | 12/2000 | Kuras et al. |
| 6,165,218 A | 12/2000 | Husson et al. |
| 6,176,882 B1 | 1/2001 | Biedermann et al. |
| 6,179,874 B1 | 1/2001 | Cauthen |
| 6,183,471 B1 | 2/2001 | Zucherman et al. |
| 6,190,387 B1 | 2/2001 | Zucherman et al. |
| 6,190,413 B1 * | 2/2001 | Sutcliffe .................. 623/17.11 |
| 6,190,414 B1 | 2/2001 | Young et al. |
| 6,193,757 B1 | 2/2001 | Foley et al. |
| 6,206,922 B1 | 3/2001 | Zdeblick et al. |
| 6,210,412 B1 | 4/2001 | Michelson |
| 6,224,595 B1 | 5/2001 | Michelson |
| 6,224,607 B1 | 5/2001 | Michelson .................. 606/96 |
| 6,224,631 B1 | 5/2001 | Kohrs |
| 6,228,118 B1 | 5/2001 | Gordon |
| 6,231,609 B1 | 5/2001 | Mehdizadeh |
| 6,234,705 B1 | 5/2001 | Troxell |
| 6,235,030 B1 | 5/2001 | Zucherman et al. |
| 6,238,397 B1 | 5/2001 | Zucherman et al. |
| 6,241,769 B1 | 6/2001 | Nicholson et al. |
| 6,241,770 B1 * | 6/2001 | Michelson .................. 623/17.11 |
| 6,241,771 B1 | 6/2001 | Gresser et al. |
| 6,245,072 B1 | 6/2001 | Zdeblick et al. |
| 6,245,108 B1 | 6/2001 | Biscup |
| 6,258,125 B1 | 7/2001 | Paul .................. 623/17.11 |
| 6,261,296 B1 | 7/2001 | Aebi et al. |
| 6,264,655 B1 | 7/2001 | Pisharodi |
| 6,264,656 B1 | 7/2001 | Michelson |
| 6,264,695 B1 | 7/2001 | Stoy |
| 6,270,498 B1 | 8/2001 | Michelson |
| 6,277,149 B1 | 8/2001 | Boyle et al. |
| 6,280,444 B1 | 8/2001 | Zucherman et al. |
| 6,280,475 B1 | 8/2001 | Bao et al. |
| 6,287,343 B1 | 9/2001 | Kuslich et al. |
| 6,296,664 B1 | 10/2001 | Middleton |
| 6,296,665 B1 | 10/2001 | Strnad et al. |
| 6,302,914 B1 | 10/2001 | Michelson |

| Patent No. | Date | Inventor |
|---|---|---|
| 6,309,421 B1 | 10/2001 | Pisharodi |
| 6,311,562 B1 | 11/2001 | Hanada |
| 6,315,795 B1 | 11/2001 | Scarborough et al. |
| 6,315,797 B1 | 11/2001 | Middleton |
| 6,325,827 B1 | 12/2001 | Lin |
| 6,332,882 B1 | 12/2001 | Zucherman et al. |
| 6,332,883 B1 | 12/2001 | Zucherman et al. |
| 6,342,074 B1 | 1/2002 | Simpson |
| 6,348,071 B1 | 2/2002 | Steffee et al. |
| 6,350,283 B1 | 2/2002 | Michelson |
| 6,364,880 B1 | 4/2002 | Michelson |
| 6,368,350 B1 | 4/2002 | Erickson et al. |
| 6,368,351 B1 | 4/2002 | Glenn et al. |
| 6,371,984 B1 | 4/2002 | Van Dyke et al. |
| 6,371,988 B1 | 4/2002 | Pafford et al. |
| 6,371,989 B1 | 4/2002 | Chauvin et al. |
| 6,379,355 B1 | 4/2002 | Zucherman et al. |
| 6,379,385 B1 | 4/2002 | Kalas et al. |
| 6,383,221 B1 | 5/2002 | Scarborough et al. |
| 6,391,030 B1 | 5/2002 | Wagner et al. |
| 6,391,058 B1 | 5/2002 | Kuslich et al. |
| 6,395,030 B1 | 5/2002 | Songer et al. |
| 6,395,031 B1 | 5/2002 | Foley et al. |
| 6,395,032 B1 | 5/2002 | Gauchet |
| 6,395,034 B1 | 5/2002 | Suddaby |
| 6,402,785 B1 * | 6/2002 | Zdeblick et al. .......... 623/17.16 |
| 6,409,766 B1 | 6/2002 | Brett |
| 6,413,278 B1 | 7/2002 | Marchosky |
| 6,416,551 B1 | 7/2002 | Keller |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,425,920 B1 | 7/2002 | Hamada |
| 6,432,106 B1 | 8/2002 | Fraser |
| 6,432,107 B1 * | 8/2002 | Ferree ........................ 606/247 |
| 6,436,098 B1 | 8/2002 | Michelson |
| 6,436,119 B1 | 8/2002 | Erb et al. |
| 6,436,140 B1 | 8/2002 | Liu et al. |
| 6,436,142 B1 | 8/2002 | Paes et al. |
| 6,440,168 B1 | 8/2002 | Cauthen |
| 6,440,169 B1 | 8/2002 | Elberg et al. |
| 6,443,990 B1 | 9/2002 | Aebi et al. |
| 6,447,512 B1 | 9/2002 | Landry et al. |
| 6,447,544 B1 | 9/2002 | Michelson |
| 6,447,547 B1 | 9/2002 | Michelson |
| 6,451,019 B1 | 9/2002 | Zucherman et al. |
| 6,451,020 B1 | 9/2002 | Zucherman et al. |
| 6,454,804 B1 | 9/2002 | Ferree |
| 6,454,807 B1 | 9/2002 | Jackson |
| 6,458,131 B1 | 10/2002 | Ray |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B2 | 10/2002 | Zdeblick et al. |
| 6,475,219 B1 | 11/2002 | Shelokov |
| 6,478,796 B2 | 11/2002 | Zucherman et al. |
| 6,478,822 B1 | 11/2002 | Leroux et al. |
| 6,478,823 B1 | 11/2002 | Michelson |
| 6,482,233 B1 | 11/2002 | Aebi et al. |
| 6,482,235 B1 | 11/2002 | Lambrecht et al. |
| 6,485,517 B1 | 11/2002 | Michelson |
| 6,488,710 B2 | 12/2002 | Besselink |
| 6,500,178 B2 | 12/2002 | Zucherman et al. |
| 6,500,205 B1 | 12/2002 | Michelson |
| 6,503,279 B1 | 1/2003 | Webb et al. |
| 6,514,256 B2 | 2/2003 | Zucherman et al. |
| 6,517,580 B1 * | 2/2003 | Ramadan et al. ......... 623/17.15 |
| 6,520,993 B2 | 2/2003 | James et al. |
| 6,520,996 B1 | 2/2003 | Manasas et al. |
| 6,524,312 B2 | 2/2003 | Landry et al. |
| 6,527,773 B1 | 3/2003 | Lin et al. |
| 6,527,804 B2 | 3/2003 | Gauchet |
| 6,527,806 B2 | 3/2003 | Ralph et al. |
| 6,530,933 B1 | 3/2003 | Yeung et al. |
| 6,530,955 B2 | 3/2003 | Boyle et al. |
| 6,540,785 B1 | 4/2003 | Gill et al. |
| 6,547,823 B2 | 4/2003 | Scarborough et al. |
| 6,548,002 B2 | 4/2003 | Gresser et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett et al. |
| 6,569,201 B2 | 5/2003 | Moumene et al. |
| 6,572,653 B1 | 6/2003 | Simonson |
| 6,572,654 B1 | 6/2003 | Santilli |
| 6,575,982 B1 | 6/2003 | Bonutti |
| 6,576,016 B1 | 6/2003 | Hochshuler et al. |
| 6,576,017 B2 | 6/2003 | Foley et al. |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B2 | 6/2003 | Dorchak et al. |
| 6,582,468 B1 | 6/2003 | Gauchet |
| 6,607,558 B2 * | 8/2003 | Kuras ...................... 623/17.16 |
| 6,626,944 B1 | 9/2003 | Taylor |
| 6,682,561 B2 * | 1/2004 | Songer et al. ............ 623/17.11 |
| 6,682,562 B2 * | 1/2004 | Viart et al. ............... 623/17.14 |
| 6,699,246 B2 | 3/2004 | Zucherman et al. |
| 6,706,068 B2 * | 3/2004 | Ferree ...................... 623/17.11 |
| 6,706,070 B1 | 3/2004 | Wagner et al. |
| 6,740,118 B2 * | 5/2004 | Eisermann et al. ....... 623/17.14 |
| 6,749,635 B1 * | 6/2004 | Bryan ...................... 623/17.16 |
| 6,755,841 B2 | 6/2004 | Fraser et al. |
| 6,770,095 B2 | 8/2004 | Grinberg |
| 6,793,678 B2 * | 9/2004 | Hawkins ................... 623/17.15 |
| 6,887,248 B2 * | 5/2005 | McKinley et al. ............. 606/99 |
| 6,890,355 B2 * | 5/2005 | Michelson ............... 623/17.11 |
| 6,936,071 B1 * | 8/2005 | Marnay et al. ........... 623/17.15 |
| 6,966,929 B2 * | 11/2005 | Mitchell .................. 623/17.11 |
| 7,048,766 B2 * | 5/2006 | Ferree ...................... 623/17.16 |
| 7,056,344 B2 * | 6/2006 | Huppert et al. ........... 623/17.16 |
| 7,063,725 B2 * | 6/2006 | Foley ....................... 623/17.16 |
| 7,083,649 B2 * | 8/2006 | Zucherman et al. ....... 623/17.11 |
| 7,105,024 B2 * | 9/2006 | Richelsoph ............... 623/17.13 |
| 7,118,580 B1 * | 10/2006 | Beyersdorff et al. ........... 606/99 |
| 7,198,644 B2 * | 4/2007 | Schultz et al. ............ 623/17.15 |
| 7,273,496 B2 * | 9/2007 | Mitchell .................. 623/17.14 |
| 7,303,584 B2 * | 12/2007 | Castro et al. ............. 623/17.16 |
| 7,320,707 B2 * | 1/2008 | Zucherman et al. ....... 623/17.14 |
| 2001/0012938 A1 | 8/2001 | Zucherman |
| 2002/0045904 A1 * | 4/2002 | Fuss et al. ...................... 606/99 |
| 2002/0128715 A1 | 9/2002 | Bryan et al. |
| 2003/0191534 A1 * | 10/2003 | Viart et al. ............... 623/17.15 |
| 2003/0208273 A1 * | 11/2003 | Eisermann et al. ........ 623/17.14 |
| 2004/0024462 A1 * | 2/2004 | Ferree et al. .............. 623/17.14 |
| 2004/0073312 A1 * | 4/2004 | Eisermann et al. ........ 623/17.14 |
| 2004/0073313 A1 | 4/2004 | Link et al. |
| 2004/0106998 A1 | 6/2004 | Ferree |
| 2004/0117022 A1 * | 6/2004 | Marnay et al. ........... 623/17.16 |
| 2004/0138750 A1 * | 7/2004 | Mitchell .................. 623/17.11 |
| 2004/0143332 A1 * | 7/2004 | Krueger et al. ........... 623/17.14 |
| 2004/0215198 A1 * | 10/2004 | Marnay et al. ................ 606/86 |
| 2004/0225360 A1 | 11/2004 | Malone |
| 2004/0225365 A1 * | 11/2004 | Eisermann et al. ........ 623/17.15 |
| 2004/0225366 A1 | 11/2004 | Eisermann |
| 2004/0230307 A1 * | 11/2004 | Eisermann ............... 623/17.11 |
| 2005/0021145 A1 * | 1/2005 | de Villiers et al. ........ 623/17.14 |

| | | | | | | |
|---|---|---|---|---|---|---|
| 2005/0043800 A1* | 2/2005 | Paul et al. ............... 623/17.15 | WO | WO 99/26562 | | 6/1999 |
| 2005/0043802 A1* | 2/2005 | Eisermann et al. ....... 623/17.16 | WO | WO 99/59669 | | 11/1999 |
| 2005/0065611 A1* | 3/2005 | Huppert et al. .......... 623/17.15 | WO | WO 00/04851 | | 2/2000 |
| 2005/0102029 A1* | 5/2005 | Blain ....................... 623/17.13 | WO | WO 00/13619 | | 3/2000 |
| 2005/0113926 A1* | 5/2005 | Zucherman et al. ...... 623/17.14 | WO | WO 00/13620 | | 3/2000 |
| 2005/0125061 A1* | 6/2005 | Zucherman et al. ...... 623/17.11 | WO | WO 00/23015 | A1 | 4/2000 |
| 2005/0125065 A1* | 6/2005 | Zucherman et al. ...... 623/17.15 | WO | WO 01/01893 | A1 | 1/2001 |
| 2005/0154462 A1* | 7/2005 | Zucherman et al. ...... 623/17.15 | WO | WO 01/89428 | A2 | 11/2001 |
| 2005/0159818 A1* | 7/2005 | Blain ....................... 623/17.15 | | | | |
| 2005/0256579 A1* | 11/2005 | Keller et al. ............. 623/17.15 | | | | |
| 2005/0267581 A1* | 12/2005 | Marnay et al. ........... 623/17.14 | | | | |
| 2005/0283243 A1* | 12/2005 | Zucherman et al. ...... 623/17.15 | | | | |
| 2006/0004377 A1* | 1/2006 | Keller ........................ 606/99 | | | | |
| 2006/0069441 A1* | 3/2006 | Zucherman et al. ...... 623/17.15 | | | | |
| 2006/0116769 A1* | 6/2006 | Marnay et al. ........... 623/17.15 | | | | |
| 2007/0208345 A1* | 9/2007 | Marnay et al. ................ 606/61 | | | | |

FOREIGN PATENT DOCUMENTS

| | | |
|---|---|---|
| DE | 4012622 | 7/1991 |
| EP | 0307241 B1 | 3/1989 |
| FR | 2707864 | 1/1995 |
| FR | 2717066 | 9/1995 |
| FR | 2717068 | 9/1995 |
| FR | 2730156 A1 | 8/1996 |
| FR | 2780269 A1 | 12/1999 |
| FR | 2806614 A1 | 9/2001 |
| WO | WO 90/00037 | 1/1990 |
| WO | WO 95/31158 A | 11/1995 |

OTHER PUBLICATIONS

*Ceramic Interspinous Block (CISB) Assisted Anterior Interbody Fusion*, Haruo Tsuji, Norikazu Hirano, Yoshiharu Katoh, Hiroshi Ohsima, Hirokazu Ishihara, Hisao Matsui,and Yohihiko Hayashi, *Journal of Spinal Disorders* vol. 3. No. 1, pp. 77-86, c1990 Raven Press, Ltd., New York.

*Instrumentation and Implants for Spinal Surgery,*J. Dabb, *Diary of the XVIIIth Scientific Meeting of the PTO Tr/Pamietnik XVIII Zjazdu Naukowego PTO Tr/PZ,WL, Warszawa,* Link America Inc., 1971, 665.

*Spinal Stenosis and Neurogenic Claudication*, Richard W. Porter, MD, FRCS, FRCSE, *SPINE* vol. 21, No. 17, pp. 2046-2052, c1996, Lippincott-Raven Publishers.

*Preliminary Design and Experimental Studies of a Novel Soft Implant for Correcting Sagittal Plan Instability in the Lumbar Spine*, R.J.Minns, BEng, Msc, PhD, DscTech, and W.K.Walsh, FRCS, *SPINE* vol. 22, No. 16, pp. 1819-1827, c1997, Lippincott-Raven Publishers.

* cited by examiner

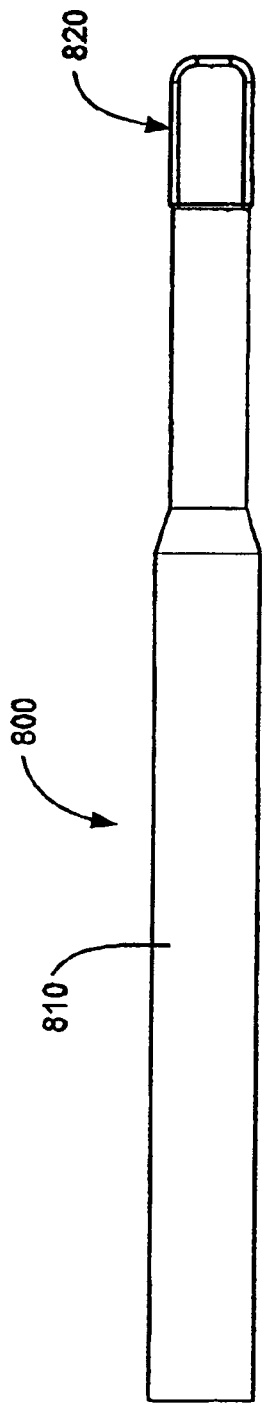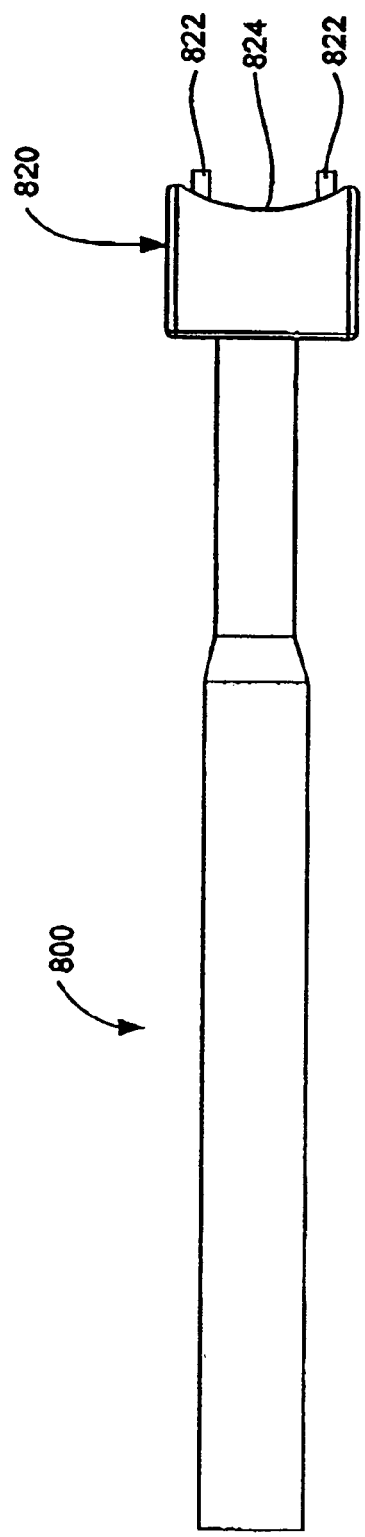
FIG. - 8A
FIG. - 8B

US 7,503,935 B2

METHOD OF LATERALLY INSERTING AN ARTIFICIAL VERTEBRAL DISK REPLACEMENT WITH TRANSLATING PIVOT POINT

CLAIM OF PRIORITY

This application claims priority under 35 U.S.C. 119 to U.S. patent application Ser. No. 60/526,724, filed on Dec. 2, 2003 and entitled "ARTIFICIAL VERTEBRAL DISK REPLACEMENT IMPLANT WITH TRANSLATING PIVOT POINT AND LATERAL IMPLANT METHOD," which is hereby incorporated by reference.

CROSS-REFERENCE TO RELATED APPLICATIONS

This application is related to U.S. Provisional Application No. 60/422,039, filed Oct. 29, 2002, entitled "ARTIFICIAL VERTEBRAL DISK REPLACEMENT IMPLANT WITH TRANSLATING PIVOT POINT AND METHOD", U.S. patent application Ser. No. 10/684,668, filed Oct. 14, 2003, entitled "ARTIFICIAL VERTEBRAL DISK REPLACEMENT IMPLANT WITH CROSSBAR SPACER AND METHOD", U.S. patent application Ser. No. 10/684,669, filed Oct. 14,2003, entitled "ARTIFICIAL VERTEBRAL DISK REPLACEMENT IMPLANT WITH TRANSLATING PIVOT POINT AND METHOD", U.S. Provisional Application No. 60/422,011, filed Oct. 29, 2002, entitled "TOOLS FOR IMPLANTING AN ARTIFICIAL VERTEBRAL DISK AND METHOD", U.S. patent application Ser. No. 10/685,134, filed Oct. 14, 2003, entitled "TOOLS FOR IMPLANTING AN ARTIFICIAL VERTEBRAL DISK AND METHOD", U.S. Provisional Application No. 60/422,022, filed Oct. 29, 2002, entitled "ARTIFICIAL VERTEBRAL DISK REPLACEMENT IMPLANT WITH A SPACER AND METHOD", U.S. Provisional Application No. 60/422,021, filed Oct. 29, 2002, entitled "ARTIFICIAL VERTEBRAL DISK REPLACEMENT IMPLANT WITH CROSSBAR SPACER AND METHOD", U.S. patent application Ser. No. 10/685,011, filed Oct. 14, 2003, entitled "ARTIFICIAL VERTEBRAL DISK REPLACEMENT IMPLANT WITH SPACER AND METHOD", U.S. patent application Ser. No. 10/981,863, filed Nov. 5, 2005, entitled "LATERALLY INSERTABLE ARTIFICIAL VERTEBRAL DISK REPLACEMENT IMPLANT WITH TRANSLATING PIVOT POINT", U.S. patent application Ser. No. 10/982,638, filed Nov. 5, 2004, entitled "LATERALLY INSERTABLE ARTIFICIAL VERTEBRAL DISK REPLACEMENT IMPLANT WITH A CROSSBAR SPACER", U.S. patent application No. 10/981,952, filed Nov. 5, 2004, entitled "METHOD OF LATERALLY INSERTING AN ARTIFICIAL VERTEBRAL DISK REPLACEMENT IMPLANT WITH A CROSSBAR SPACER", U.S. patent application No. 10/981,923, filed Nov. 5, 2004, entitled "LATERALLY INSERTABLE ARTIFICIAL VERTEBRAL DISK REPLACEMENT IMPLANT WITH A SPACER", U.S. patent application Ser. No. 10/981,945, filed Nov. 5, 2004, entitled "METHOD OF LATERALLY INSERTING AN ARTIFICIAL VERTEBRAL DISK REPLACEMENT IMPLANT WITH A SPACER", all of which are incorporated herein by reference.

FIELD OF ART

This field of art of this disclosure is directed to an artificial vertebral disk replacement and method.

BACKGROUND

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of aging. For example, with aging comes an increase in spinal stenosis (including, but not limited to, central canal and lateral stenosis), and facet joint degeneration. Spinal stenosis typically results from the thickening of the bones that make up the spinal column and is characterized by a reduction in the available space for the passage of blood vessels and nerves. Facet joint degeneration results from the constant load borne by the facet joints, and the eventual wear that results. Pain associated with both conditions can be relieved by medication and/or surgery.

In addition, to spinal stenosis, and facet joint degeneration, the incidence of damage to the intervertebral disks is also common. The primary purpose of the intervertebral disk is to act as a shock absorber. The disk is constructed of an inner gel-like structure, the nucleus pulposus (the nucleus), and an outer rigid structure comprised of collagen fibers, the annulus fibrosus (the annulus). At birth, the disk is 80% water, and then gradually diminishes with time, becoming stiff. With age, disks may degenerate, and bulge, thin, herniate, or ossify. Additionally, damage to disks may occur as a result disease, trauma or injury to the spine.

The damage to disks may call for a range of restorative procedures. If the damage is not extensive, repair may be indicated, while extensive damage may indicate full replacement. Regarding the evolution of restoration of damage to intervertebral disks, rigid fixation procedures resulting in fusion are still the most commonly performed surgical intervention. However, trends suggest a move away from such procedures. Currently, areas evolving to address the shortcomings of fusion for remediation of disk damage include technologies and procedures that preserve or repair the annulus, that replace or repair the nucleus, and that advance implants for total disk replacement. The trend away from fusion is driven both by issues concerning the quality of life for those suffering from damaged intervertebral disks, as well as responsible health care management. These issues drive the desire for procedures that are minimally invasive, can be tolerated by patients of all ages, especially seniors, and can be performed preferably on an outpatient basis.

Most recently, there has been an increased interest in total disk replacement technology. A number of artificial disks are beginning to appear in the medical device marketplace. These artificial disks vary greatly in shape, design and functionality. With these devices go tools and methods for insertion between vertebrae thereof.

Accordingly, there is a need in the art for innovation in technologies and methods that advance the art in the area of minimally invasive intervertebral disk replacement. This not only enhances the quality of life for those suffering from the condition, but is responsive to the current needs of health care management.

BRIEF DESCRIPTION OF THE DRAWINGS

FIG. 8A is a side view of an embodiment of the implant lateral insertion tool of the invention. FIG. 8B is a top view of the embodiment of the implant lateral insertion tool of the invention.

DETAILED DESCRIPTION

The following description is presented to enable any person skilled in the art to make and use what is disclosed. Various modifications to the embodiments described will be readily apparent to those skilled in the art, and the principles defined herein can be applied to other embodiments and applications without departing from the spirit and scope of what is disclosed and defined by the appended claims. Thus, what is disclosed is not intended to be limited to the embodiments shown, but is to be accorded the widest scope consistent with the principles and features disclosed herein. To the extent necessary to achieve a complete understanding of what is disclosed herein, the specification and drawings of all patents and patent applications cited in this application are incorporated herein by reference.

Figure 1A:
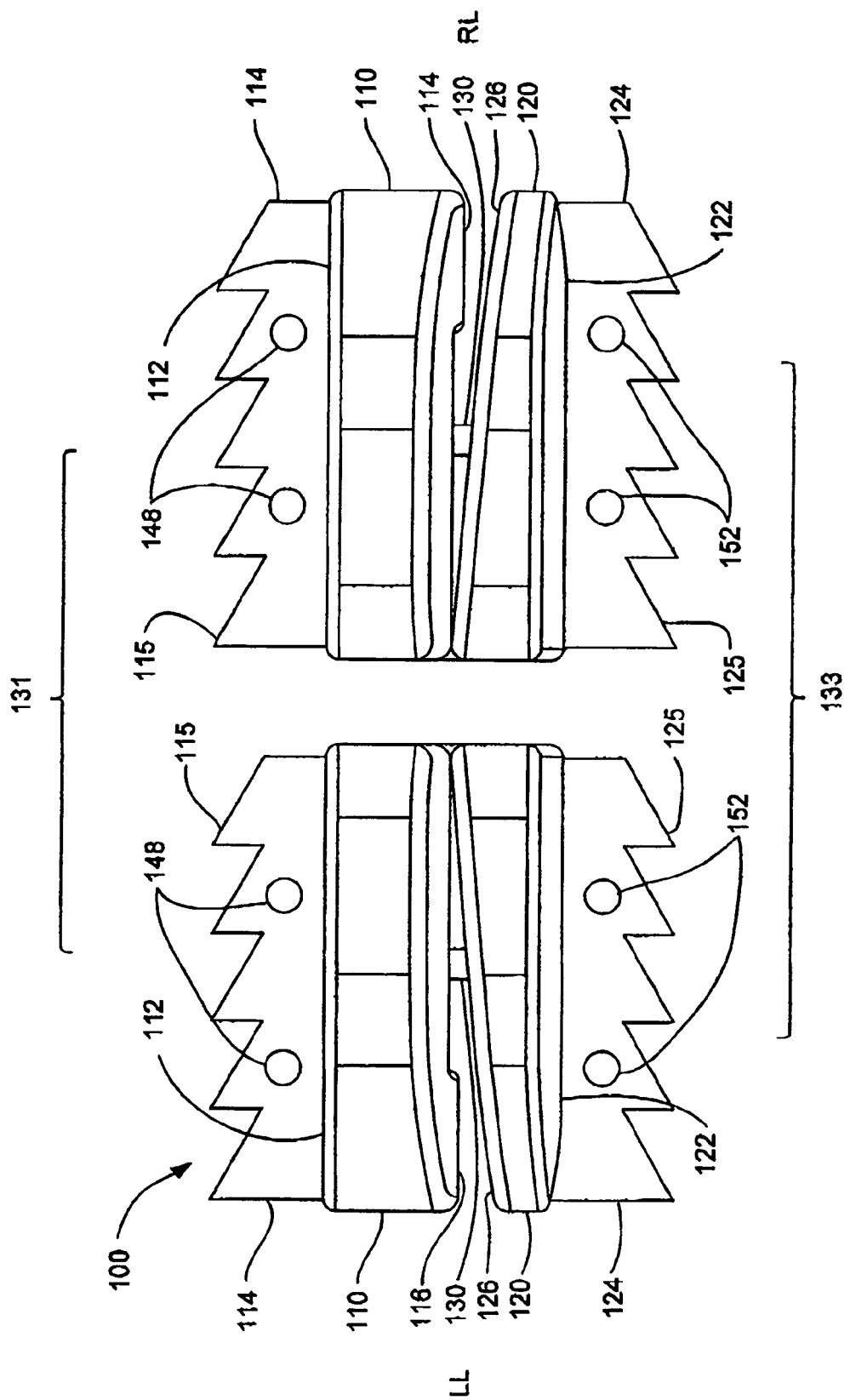
FIG. 1A is a posterior view of an embodiment of the assembled implant of the invention.

FIG. 1A shows an embodiment of the implant 100 having a four-piece configuration. The designations, "A" for anterior, "P" for posterior, "RL" for right lateral, and "LL" for left lateral are given in the drawings for spatial orientation. These designations give the relationship of all faces of embodiments of the disclosed intervertebral implant from the superior perspective; i.e. looking down the axis of the spine. The implant 100 has a pair 131 of first end plates, or upper end plates 110 that are configured to mate with a first vertebra. The upper end plate 110 of implant 100 has a first outer surface 112 from which a first keel 114 extends with a first set of teeth 115. Additionally, the implant 100 has a pair 133 of second end plates, or lower end plates 120 that are configured to mate with a second vertebra. The lower end plate 120 has a second outer surface 122 from which a keel 124 extends with a second set of teeth 125. A pair of pivoting or articulating elements or spacers 130 that are part of the pair 133 of lower end plates 120 acts as an articulating element, or spacer between the first end plate 110 and the second end plate 120 and facilitates pivotal or rotational and also twisting movement of the first end plate 110 and the second end plate 120, relative to each other. In the embodiments described, the pair of articulating elements, or spacers 130 is curved or convex, as will be discussed in more detail below.

Figure 6A:
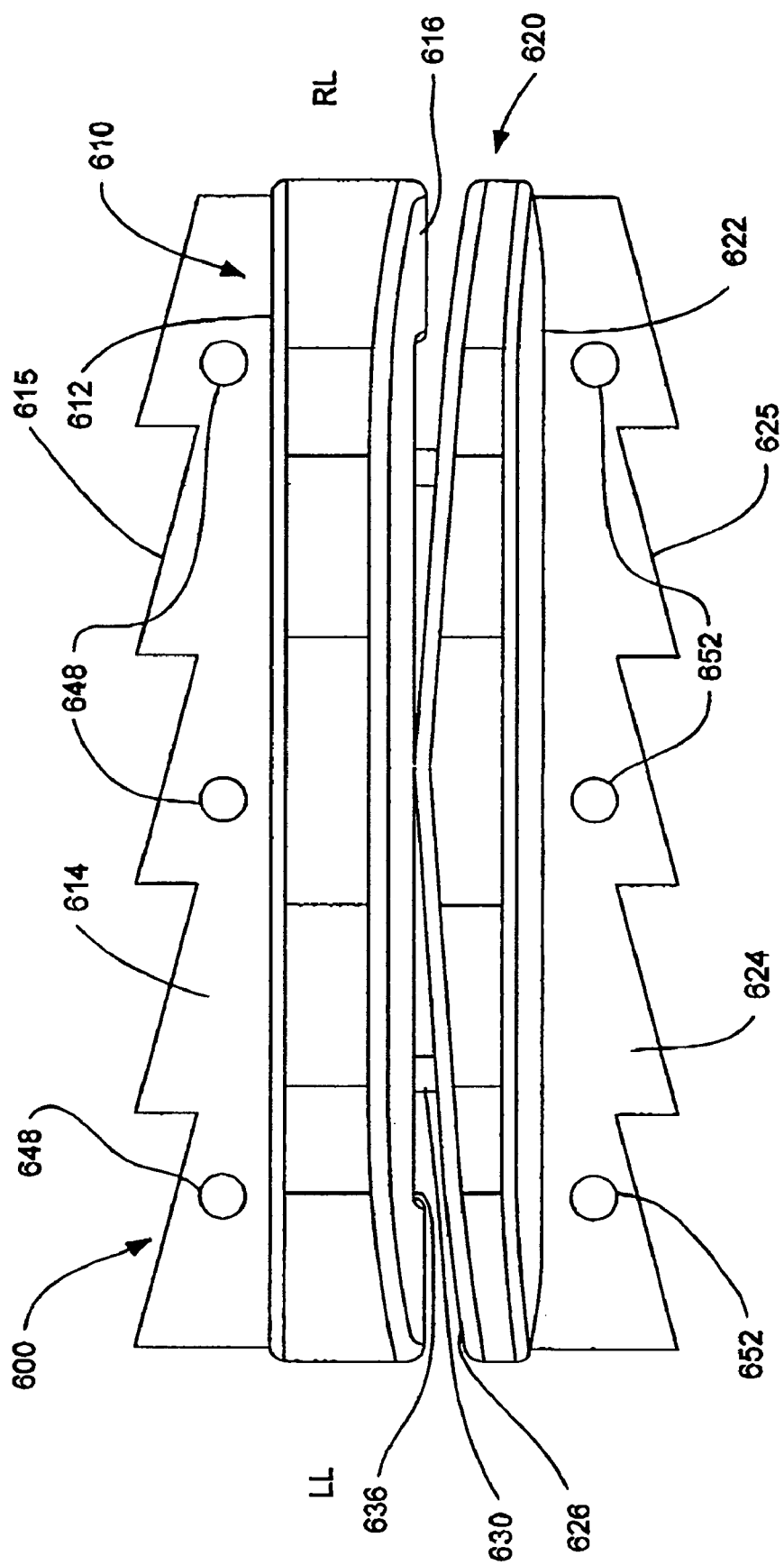
FIG. 6A is a rear view of an alternate embodiment of the invention having two plates.
Figure 6B:
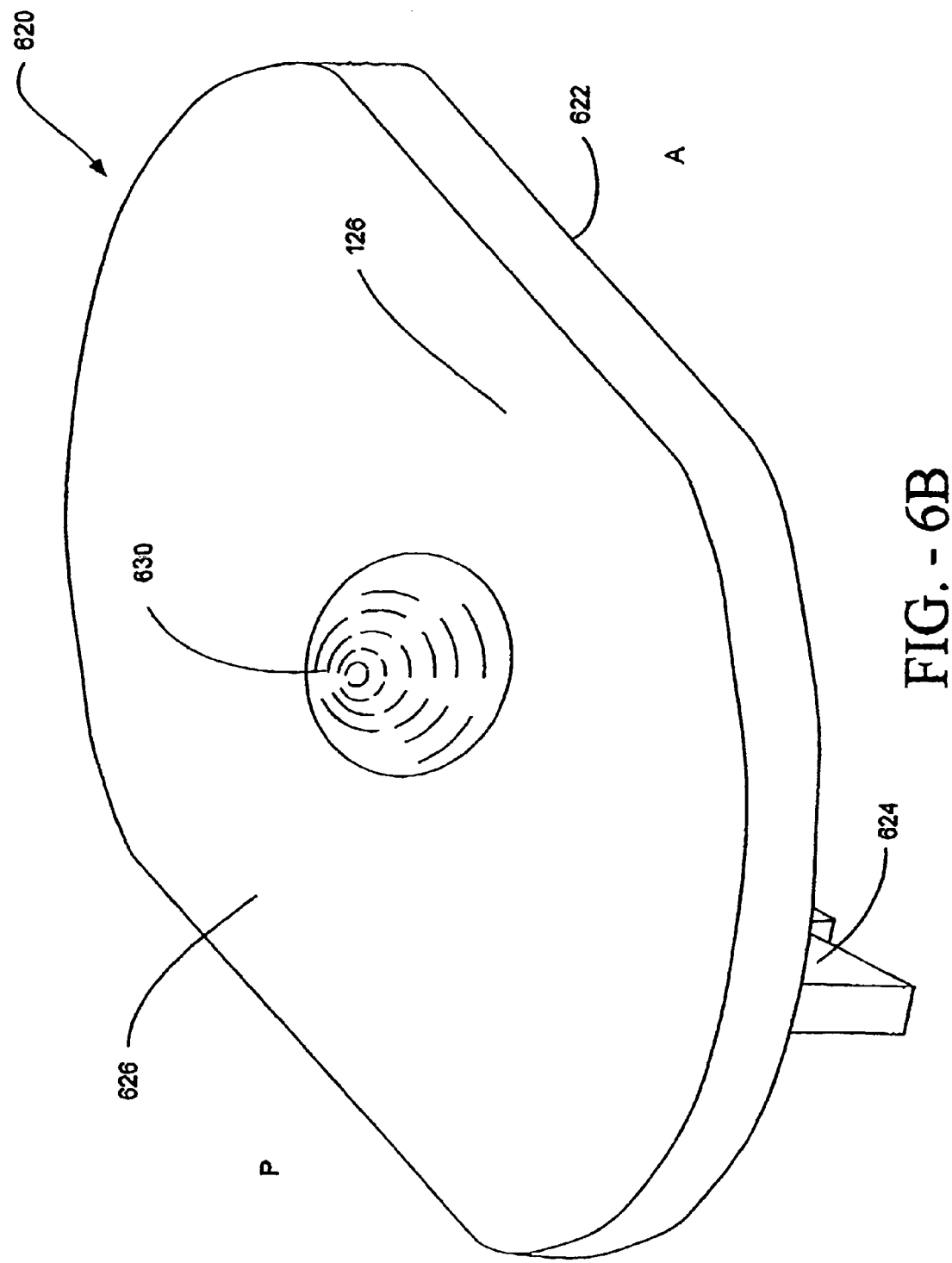
FIG. 6B and FIG. 6C show perspective views of the first and second inner surfaces of the first end plate and the second end plate of an alternative embodiment of implant 600.
Figure 6C:
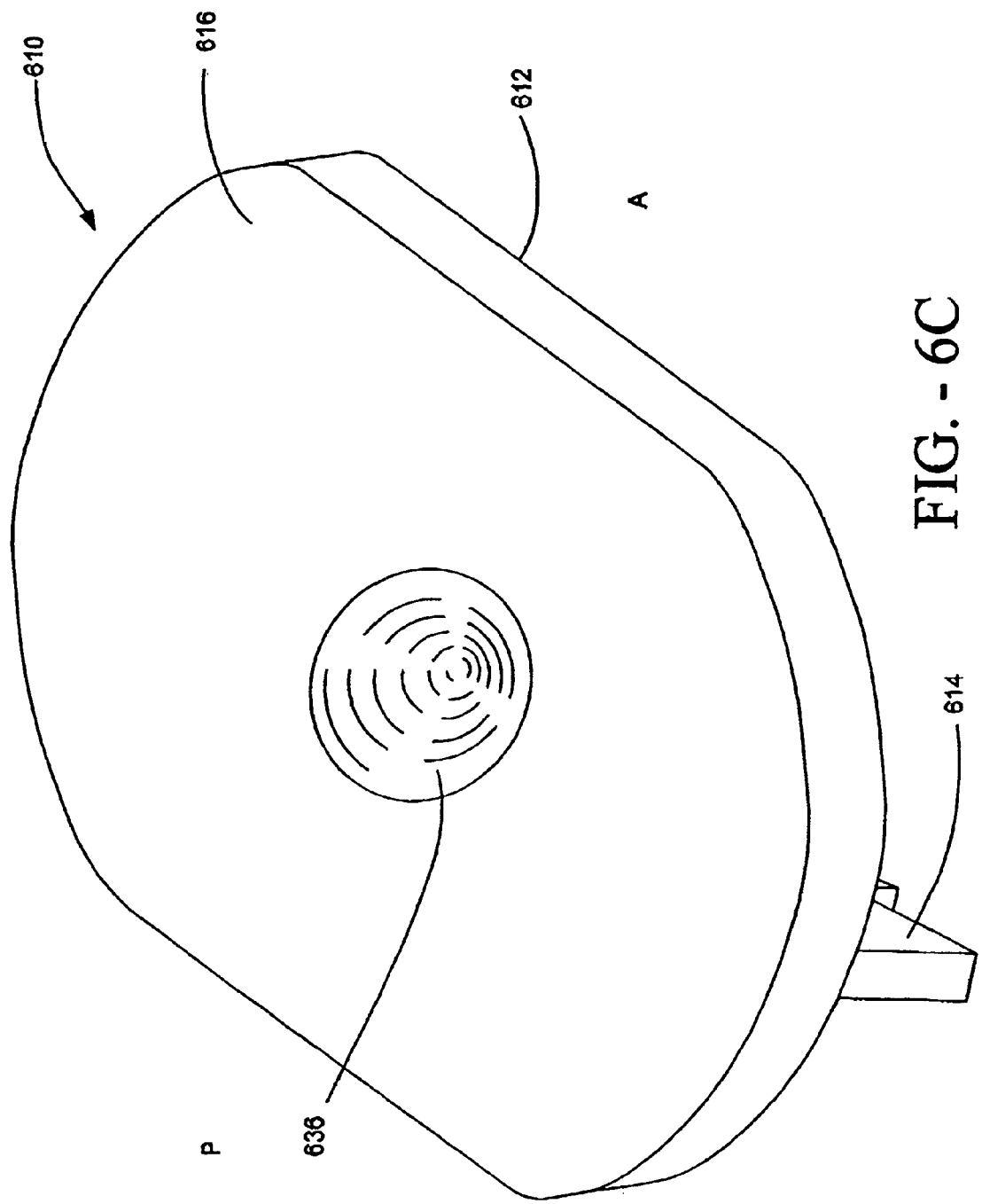
Figure 6D:
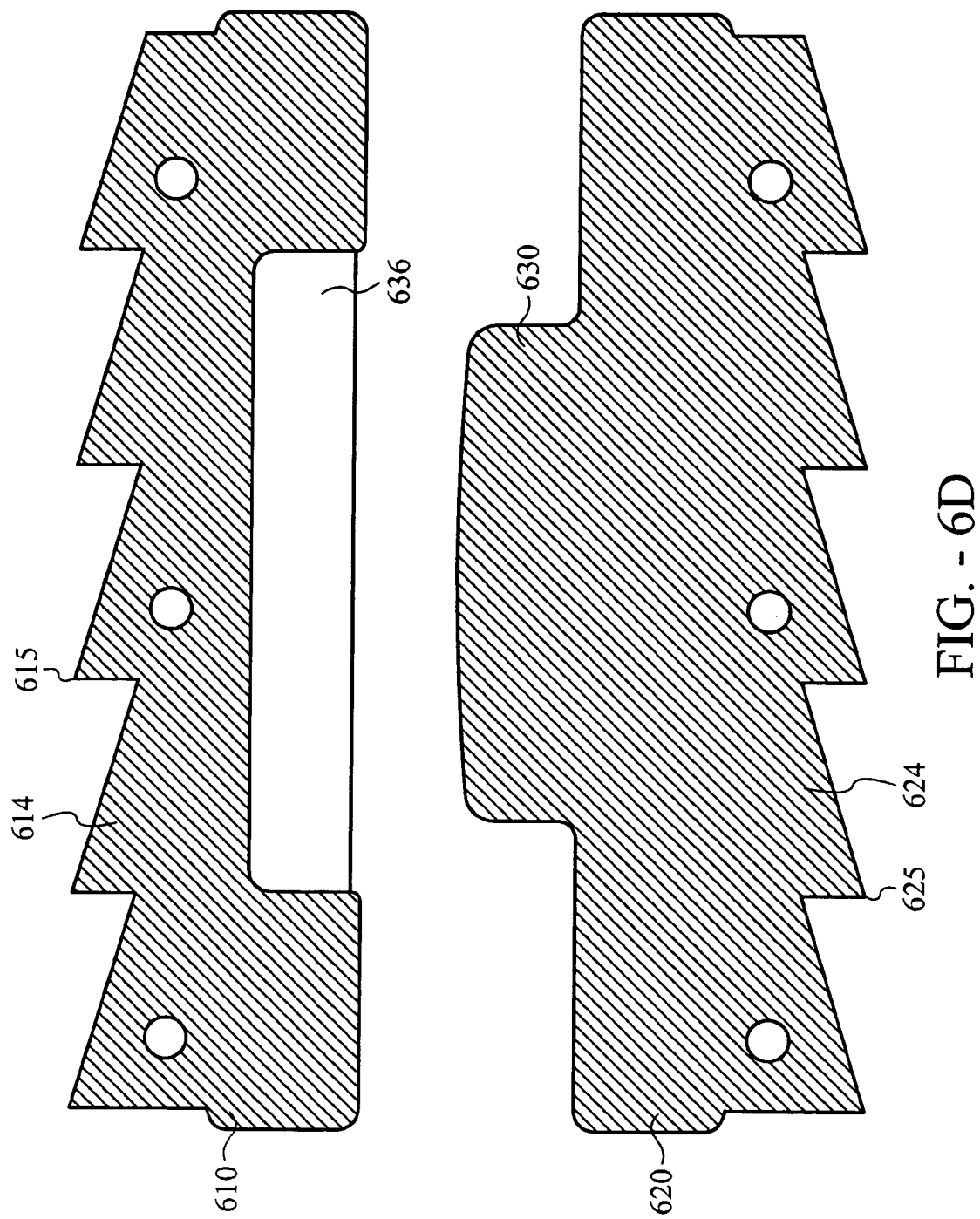
FIG. 6D is a cross sectional view of the embodiment shown in FIG. 6A.

Several configurations of implant 100 are contemplated. For instance, FIG. 6A illustrates a posterior view of an alternate embodiment of the implant shown in FIG. 1A. The implant 600 of FIG. 6A is in the form of a two-piece implant 600 having a first end plate 610 and a second end plate 620. The first end plate, or upper end plate 610 is configured to mate with a first vertebra, and a second end plate, or lower end plate 620 is configured to mate with a second vertebra. The first inner surface 616 of the upper end plate 610 has a socket or first cavity 636 formed therein. A pivoting or articulation element, or spacer 630 is formed on second end plate 620. The spacer 630 at least partially engages the first socket 636, and facilitates pivotal or rotational and also twisting movement of the first end plate 610 and the second end plate 620, relative to each other. The spacer 630 and corresponding socket 636 are dimensioned so that they are hemi-cylindrical (FIG. 6D), while in another embodiment shown in FIG. 6B and FIG. 6C, the articulating element, or spacer 630 and corresponding socket 636 are hemispherical.

The upper end plate 610 of implant 600 has a first outer surface 612 from which a first keel 614 extends with a first set of teeth 615. In one embodiment, when implant 600 is inserted between vertebrae, the first keel 614 extends longitudinally across the first outer surface 612, about perpendicular to the sagittal plane of the spine. In another embodiment, the first keel 614 extends longitudinally only partially across the first outer surface 612, about perpendicular to the sagittal plane of the spine. The teeth 615 in the two embodiments with complete or partial extension of the keel 614 across the first outer surface 612 of the upper end plate 610 point towards the left lateral face of implant 600 when the embodiment is meant to be put into a slot in a vertebral body from the left lateral approach to the spine. This orientation is shown in the figures, and is particularly evident where the keel 614 is fully displayed, as in FIG. 1A and FIG. 6A, for example. Alternatively, the teeth 615 point towards the right lateral face of implant 600 when the embodiments are meant to be put into a slot in a vertebral body from the right lateral approach to the spine.

The first outer surface 612 abuts the vertebral body when the implant 600 is implanted. The first keel 614 extends into the vertebral body to anchor implant 600 into position, and is perpendicular to the median sagittal plane of the spine, in which extension and flexion occur. The first keel 614 in this orientation offers substantial stability during extension and flexion for the implant 600 inserted between the vertebrae of a patient. Additionally, the first keel 614 in this embodiment is preferably aligned with and supports the articulation of implant 600. The first inner surface 616 with socket 636 at least partially engages the spacer 630 of the implant and opposes the second end plate 620. The first inner surface 616 can form a planar surface that is parallel to the first outer surface 612, or can form a planar surface that is not parallel to the first outer surface 612.

The lower end plate 620 has a second outer surface 622 from which a keel 624 extends with a second set of teeth 625. In one embodiment, when implant 600 is inserted between vertebrae, the second keel 624 is about perpendicular to the sagittal plane of the spine. As described above for the first upper end plate 610, in one embodiment, the second keel 624 extends longitudinally across the second outer surface 622, while in another embodiment, the second keel 624 extends longitudinally partially across the second outer surface 622. The teeth 625 in the two embodiments with complete or partial extension of the second keel 624 across the second outer surface 622 of the lower end plate 620 point towards the left lateral face of implant 600 when the embodiment is meant to be put into a slot in a vertebral body from the left lateral approach to the spine. This orientation is shown in the figures, and is particularly evident where the second keel 624 is fully displayed, as in FIG. 1A and FIG. 6A, for example. Alternatively, the teeth 625 point towards the right lateral face of implant 600 when the embodiments are meant to be put into a slot in a vertebral body from the right lateral approach to the spine.

The second outer surface 622 abuts the vertebral body when the implant 600 is implanted. The second keel 624 extends into the vertebral body to anchor implant 600 into position, and is perpendicular to the median sagittal plane of the spine, in which extension and flexion occur. The second keel 624 in this orientation offers substantial stability during extension and flexion for the implant 600 inserted between the vertebrae of a patient. Additionally, the second keel 624 in this embodiment is aligned with and supports the articulation of implant 600. The second end plate 620 with second inner surface 626 having the spacer 630 opposes the first end plate 610 with first inner surface 616 having socket 636. The spacer 630 of second inner surface 626 at least partially engages socket 636 of first upper surface. The second inner surface 626 can form a planar surface that is parallel to the second outer surface 622, or can form a planar surface that is not parallel to the second outer surface 622.

The first inner surface 616 of the first end plate 610 can be parallel to the second inner surface 626 of the second end plate 620 when the implant 600 is assembled and is in a neutral position (i.e., the position where the first end plate 610 has not rotated relative to the second end plate 620). Alternatively, the first inner surface 616 of the first end plate 610 can be non-parallel to the planar surface of the second inner surface 626 of the second end plate 620 when the implant 600 is assembled and in a neutral position. This non-parallel orientation of the first end plate 610 and the second end plate 620 allows the plates to pivot to a greater degree with respect to each other. Additionally, factors such as the height and position of the spacer 630, and the, can also be adjusted in order to increase the degree that the first end plate 610 and the second end plate 620 can pivot relative to each other. Other factors that effect the degree of movement of the first end plates 110 or 610 relative to the second end plates 120 or 620 for implant 100 or implant 600 will discussed below.

When implant 600 is inserted between vertebrae the planar surfaces corresponding to the first and second outer surfaces 612, 622 and the first and second inner surfaces 616, 626 of the first and second end plates 610, 620 lie within, or substantially within, the axial plane of the body. Similarly, the first and second keels 614, 624 are aligned in the axial plane, or perpendicular to the sagittal plane of the vertebrae. The first and second keels 614,624 extend into the vertebral bodies to anchor implant 600 into position, and are perpendicular to the median sagittal plane of the spine, in which extension and flexion occur. The first and second keels 614,624 in this orientation offer substantial stability during extension and flexion for implant 600 inserted between the vertebrae of a patient. Additionally, the first and second keels 614,624 in this embodiment are aligned with and support the axis of articulation of implant 600 defined by an RL to LL orientation.

The lateral orientation of the keels allow the implants to be inserted into the spine using a lateral approach as opposed to an anterior or posterior approach. The lateral approach is advantageous, because the spinal nerves in the spinal cavity are minimally undisturbed when the implants are inserted laterally into the spine. In comparison to a posterior insertion approach in which the spinal nerves can be substantially disturbed, the spinal nerves are bypassed and relatively undisturbed when the implant is inserted laterally between the vertebral bodies from the side of the spine. Although an anterior insertion approach has its benefits, the lateral insertion approach can allow the present implant and associated implantation tools, to be inserted into the spine with less disturbance of the patient's internal organs. This can translate into less time and risk associated with preparing the spine for insertion as well as inserting the implant itself into the spine. Further, the laterally oriented keels offer substantial stability to the vertebral bodies during extension, flexion and lateral bending of the spine.

In the embodiment shown in FIG. 1A and FIG. 6A, the first and second keels 114,124 and 614,624 include ports 148,152 and 648,652, respectively, that facilitate bone ingrowth. For example, bone from the vertebral bodies can grow thorough the ports 148,152 and 648,652, and aid in securing the first and second keels 114,124 and 614,624, and thereby for securing implants 100 and 600 once inserted between vertebral bodies. In addition, surfaces defined by the first and second keels 114,124 and 614,624 and the first and second outer surfaces 112,122 and 612, 622 of implants 100 and 600 can be roughened in order to promote bone ingrowth into these defined surfaces of implants 100 and 600. In other embodiments the ports 148,152 and 648,652, the first and second keels 114,124 and 614,624, and the first and second outer surfaces 112,122 and 612, 622 of implant 600 can be coated with materials that promote bone growth such as for example bone morphogenic protein, BMP, or structural materials such as hyaluronic acid, HA, or other substance which promotes growth of bone relative to and into the keels 614,624, keel ports 648,652, and other external surfaces of the implant 600.

Further, a combination of the two embodiments shown in FIG. 1A and FIG. 6A can be used to create a three-piece implant as will also be appreciated by those of ordinary skill in the art. For example, the first end plate 610 of FIG. 6A with its socket 636 from a two-piece embodiment can be combined with two second end plates 120 of FIG. 1A from a four-piece embodiment to form an implant. Similarly, the second end plate 620 with spacer 630 of a two piece embodiment, such as FIG. 6A, can be combined with two first end plates 110 from a four-piece design, such as FIG. 1A, to achieve an implant. The features described herein for an interspinous implant for lateral insertion between adjacent vertebrae are applicable to two-, three-, or four-piece embodiments. None of these configurations depart from the scope of the invention.

Figure 1B:
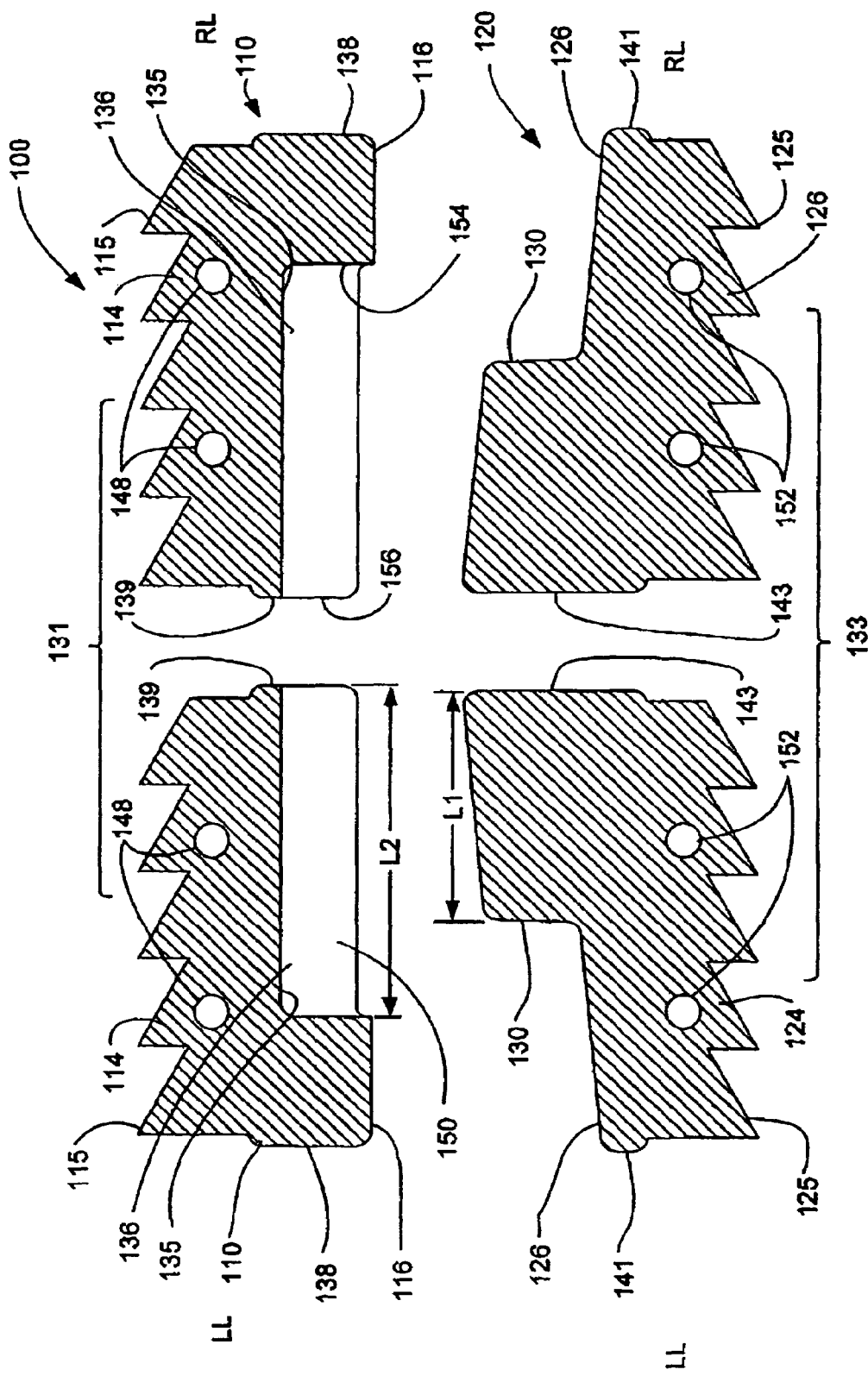
FIG. 1B is a cross-section of the device shown in FIG. 1A.

FIG. 1B depicts the pair 131 of first or upper end plates 110 and the pair 133 of second or lower end plates 120 in cross-section. Each upper and lower end plate 110, 120 has a keel 114, 124 with a set of teeth 115, 125. As for implant 600, different embodiments of implant 100 may have complete or partial extension of the first and second keels 114, 124 across the first and second outer surfaces 112, 122 of the upper and lower end plates 110, 120. The teeth 115, 125 point towards the left lateral face of implant 100 when the embodiment is meant to be put into a slot in a vertebral body from the left lateral approach to the spine, and alternatively, the teeth 115, 125 point towards the right lateral face of implant 100 when the embodiments are meant to be put into a slot in a vertebral body from the right lateral approach to the spine.

In FIG. 1B, the socket 136 formed in the first inner surface 116 of first end plate 110 has a first elongated sidewall 150, a corresponding second elongated sidewall 152 (shown in FIG. 3B), an end wall 154, and an open end 156. The open ends 156 of each of the first end plates 110 are oriented so that the open ends 156 face each other. Each of the first and second end plates 110, 120 has a first end 138, 141 and a second end 139, 143. The ends 139 of the first end plate 110 face each other, as do the ends 143 of the second end plate 120. The lower plates 120 each have an articulating element, or spacer 130, which is convex and hemi-cylindrical, that engage the socket 136. The concave hemi-cylindrical inner surface 135 of the socket 136 is sloped to allow the pair 131 of first or upper end plates 110 to easily slide, or rock, side-to-side on the articulating element, or spacer 130 and slide, or ride, forward and backward with enough looseness of fit to allow for some twisting in order to emulate the motion of the vertebral bone and intervertebral disk tissue. This arrangement, thus, has a sliding or translating pivot point. It is evident from FIG. 1B that the first and second keels 114,124 are aligned with and support the axis of articulation of the upper end plate 110 about the spacer 130 for this embodiment. This axis of articulation is longitudinally oriented with respect to the vertebrae, or about perpendicular to the sagittal plane of the spine. The alignment of the first and second keels 114,124 with the axis of articulation offers substantial stability during flexion and extension when implant 100 is inserted between the vertebrae of a patient.

Figure 1C:
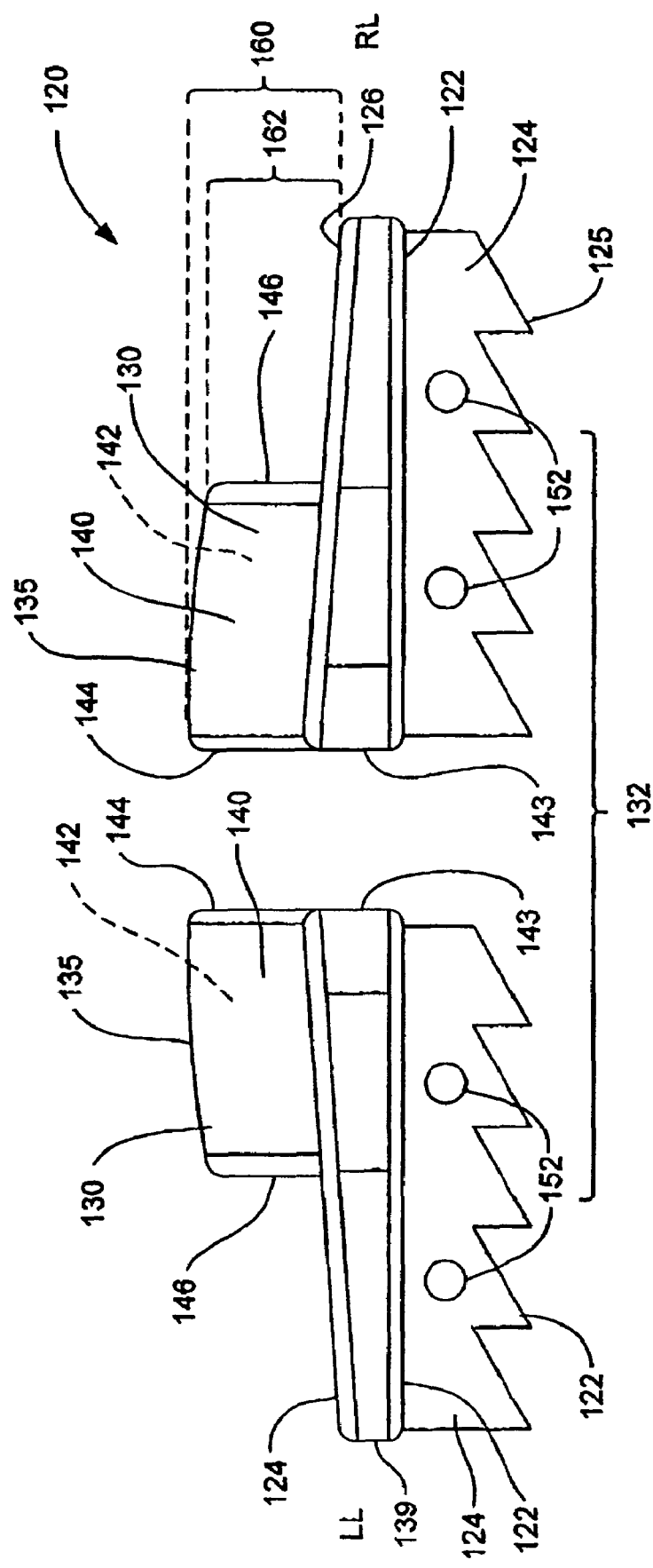
FIG. 1C is a posterior view of two bottom plates of the implant of the embodiment of the invention.

As shown in FIG. 1C, the articulating element, or spacer 130 has four sides: a first elongated sidewall 140, a second elongated sidewall 142, a third end wall 143, and a fourth end wall 146. The third end wall 144 is flush with the end 143 of the lower end plate 120 of the implant. The third end wall 144 has a profile height 160 and the fourth end wall 146 has a profile height 162. Comparing the profile heights 160, 162 to each other at the same point on the second inner surface 126 of the second end plate 120, the overall profile height of the third end wall 144 is greater than the fourth end wall 146 (i.e., 160>162). Thus, it is evident that the upper surface 135 of socket 136 slopes downwardly from the end wall 144 to the end wall 146. Together spacers 130 comprise an articulating element that has a high surface where the third end walls 144 abut each other and slope to a lower surface adjacent to fourth end walls 146.

In FIG. 1C, the edges of the articulating element or spacer 130 are eased or rounded to allow for further range of motion of the pair 131 of upper end plates 110 relative to the pair 133 of lower end plates 120. As will be appreciated by those of skill in the art, the overall height of the third end wall 144 and the fourth end wall 146 can be equivalent while still having an effective third end wall height 160 that is greater than the effective fourth end wall height 162 due to the overall slope of the second inner surface 126. Alternatively, the overall height of the third end wall 144 and the fourth end wall 146, can be different with the third end wall 144 having a height greater than the fourth end wall 146, thus eliminating the need for the second inner surface 126 to have a slope or further increasing the net difference between the height of the third end wall and the forth end wall. Further, although the spacer 130 is depicted such that the third end wall 144 is flush with the second end 143, those of skill in the art will appreciate that the spacer 130 could also be configured such that the third end wall 144 is recessed relative to the end 143 of the second end plate. In such a configuration, the third end wall 144 and the end 143 would not be flush.

Figure 1D:
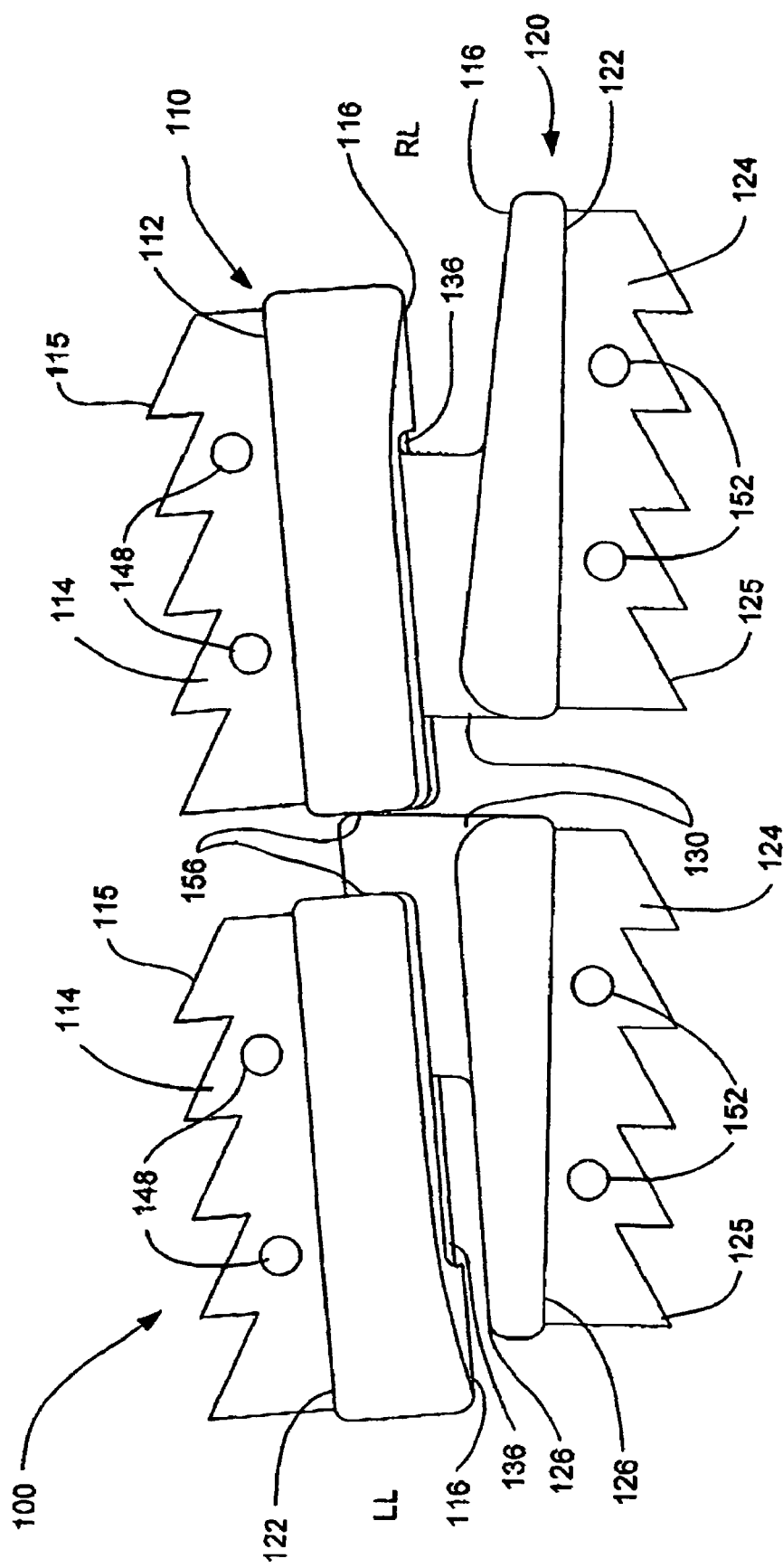
FIGS. 1D and 1E are posterior views of the embodiment of the implant of the invention shown in FIG. 1A illustrating the operation of the device in bending to the left and bending to the right, respectively.
Figure 1E:
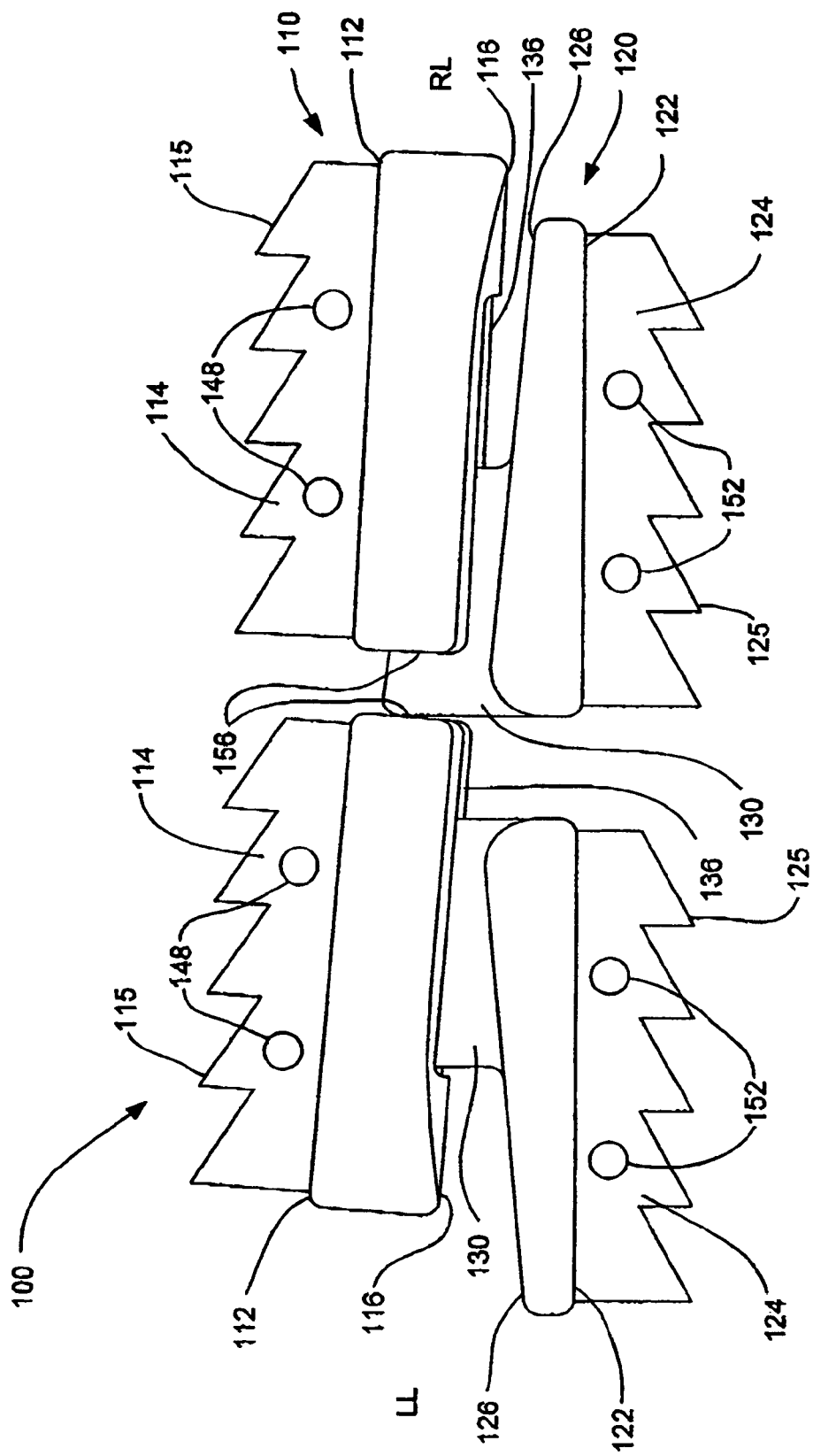

FIGS. 1D and 1E illustrate posterior views of the implant 100 showing the clearance for left and right lateral bending. Typically, left and right lateral bending ranges from 3-5°. As evident from these figures, the length of the spacer 130 can be less than the length of the socket 136. As shown, the open ends 156 of the sockets facilitate movement of the articulating elements, or spacers 130 within the socket 136 to accommodate side-bending movement.

Figure 2A:
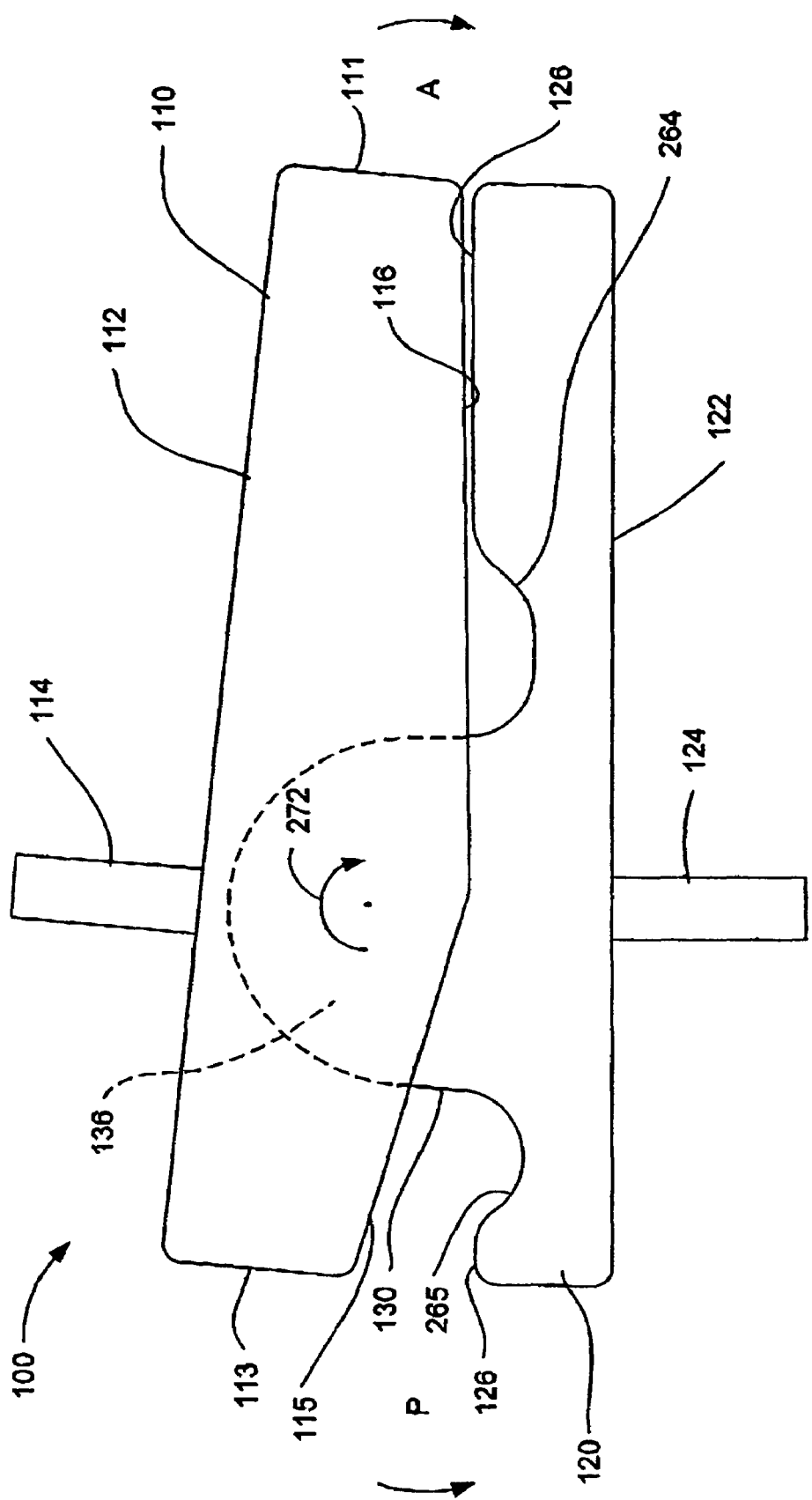
FIG. 2A is a side view of the implant of FIG. 1A showing the implant in flexion.
Figure 2B:
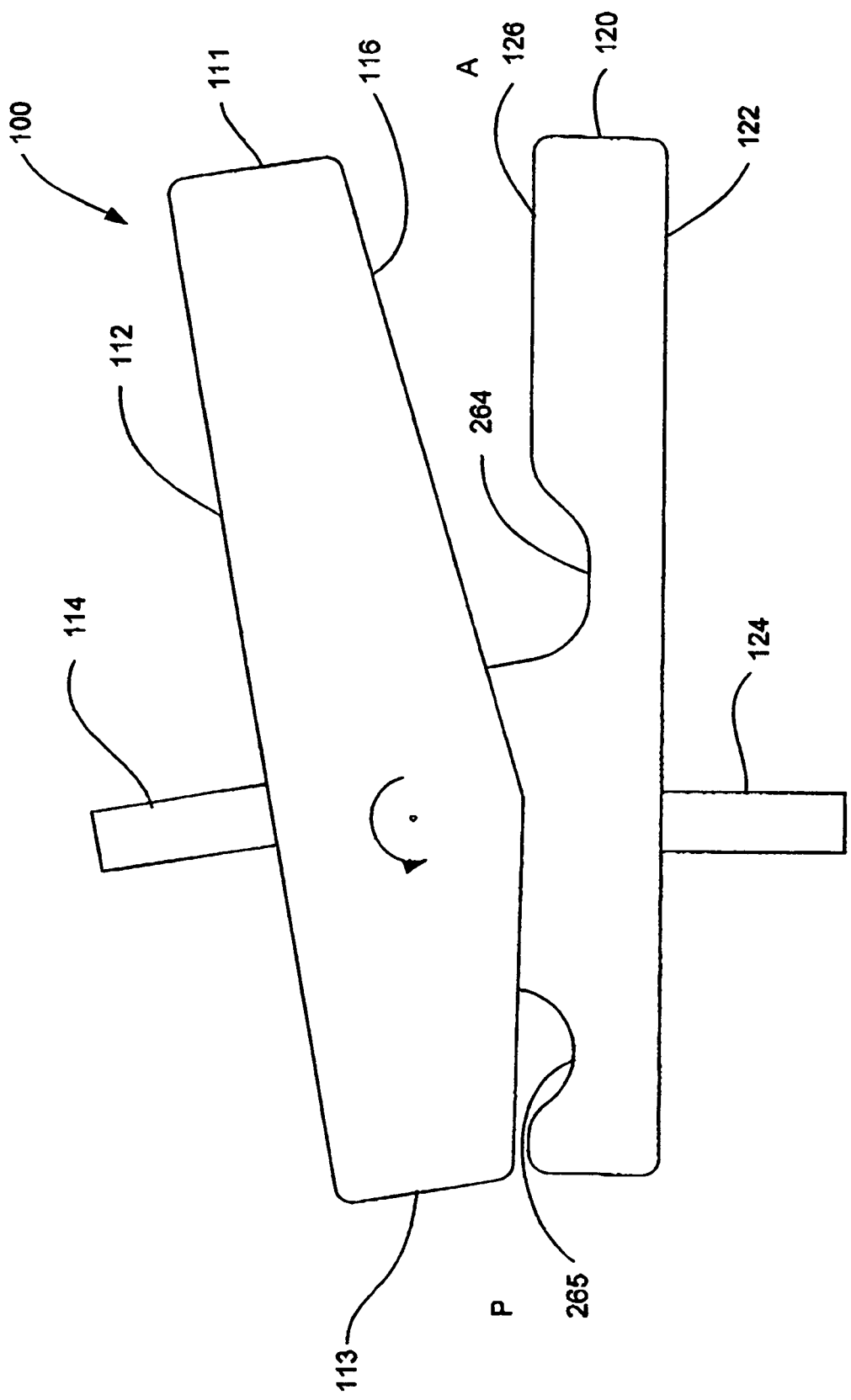
FIG. 2B is a side view of the implant showing the implant in extension.

FIG. 2A and FIG. 2B are views of the intervertebral implant 100, which depict the motion of the first end plate 110 relative to the second end plate 120. In FIG. 2A and FIG. 2B, a side view of implant 100 is depicted, showing first end plate 110 with socket 136 and the second end plate 120 with the articulating element or spacer 130. As is apparent from the figures, the sloping of the first inner surface 116 of the first end plate 110 facilitates rotation of the spacer and socket in an anterior A direction and a posterior P direction. As depicted, the first inner surface 116 slopes from a high point at about where the socket is located to low points at the ends 111 and 113 of the upper end plate 110. As shown in FIG. 2A, the implant 100 is positioned to achieve flexion (i.e., forward bending) in a range up to about 15°, but more preferably 10°, while in FIG. 2B, the implant 100 is positioned to achieve extension (i.e., backward bending) in a preferable range of up to about 5°.

Figure 2C:
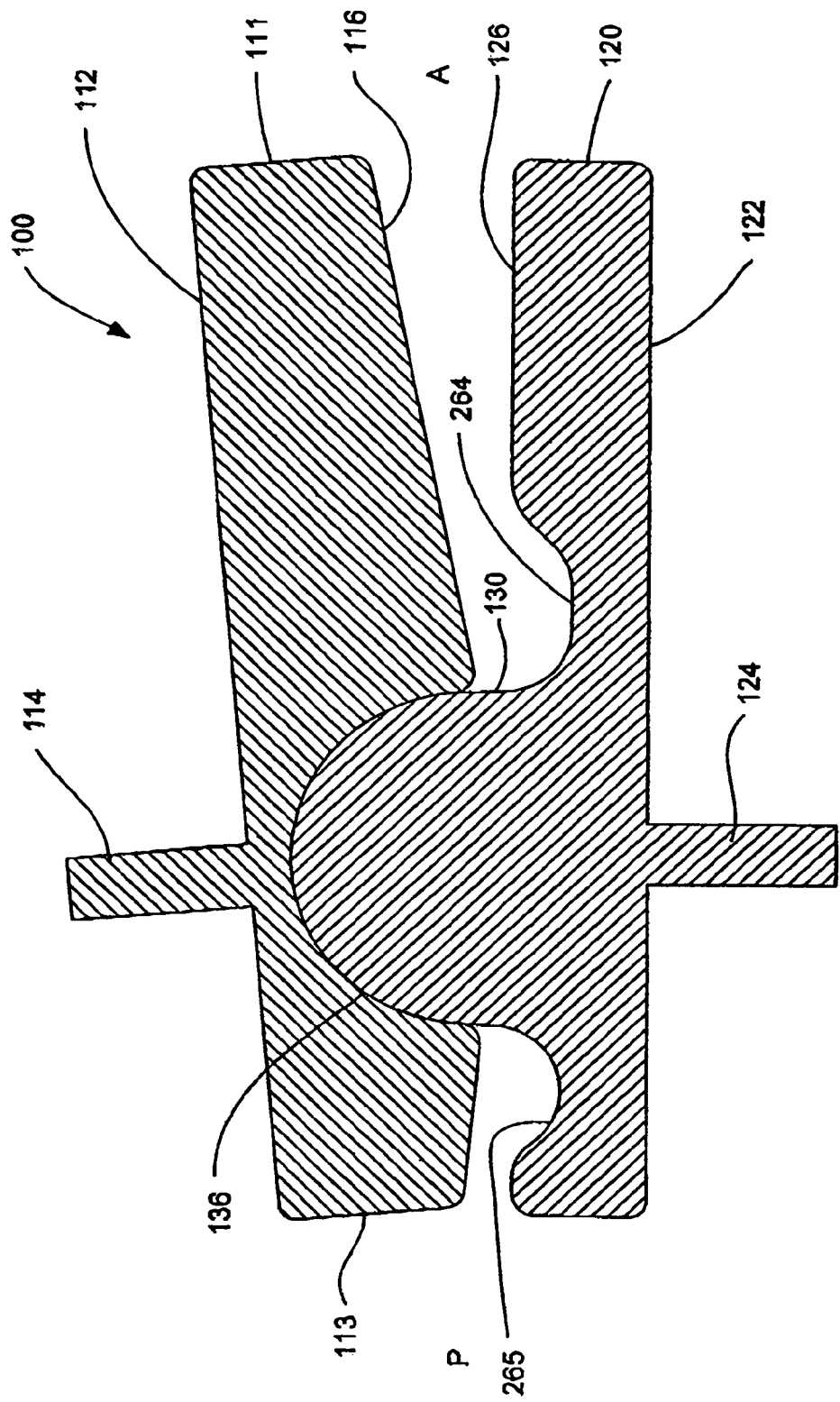
FIG. 2C is a partial cross-sectional view of a side view of the implant of an embodiment of the invention.
Figure 2D:
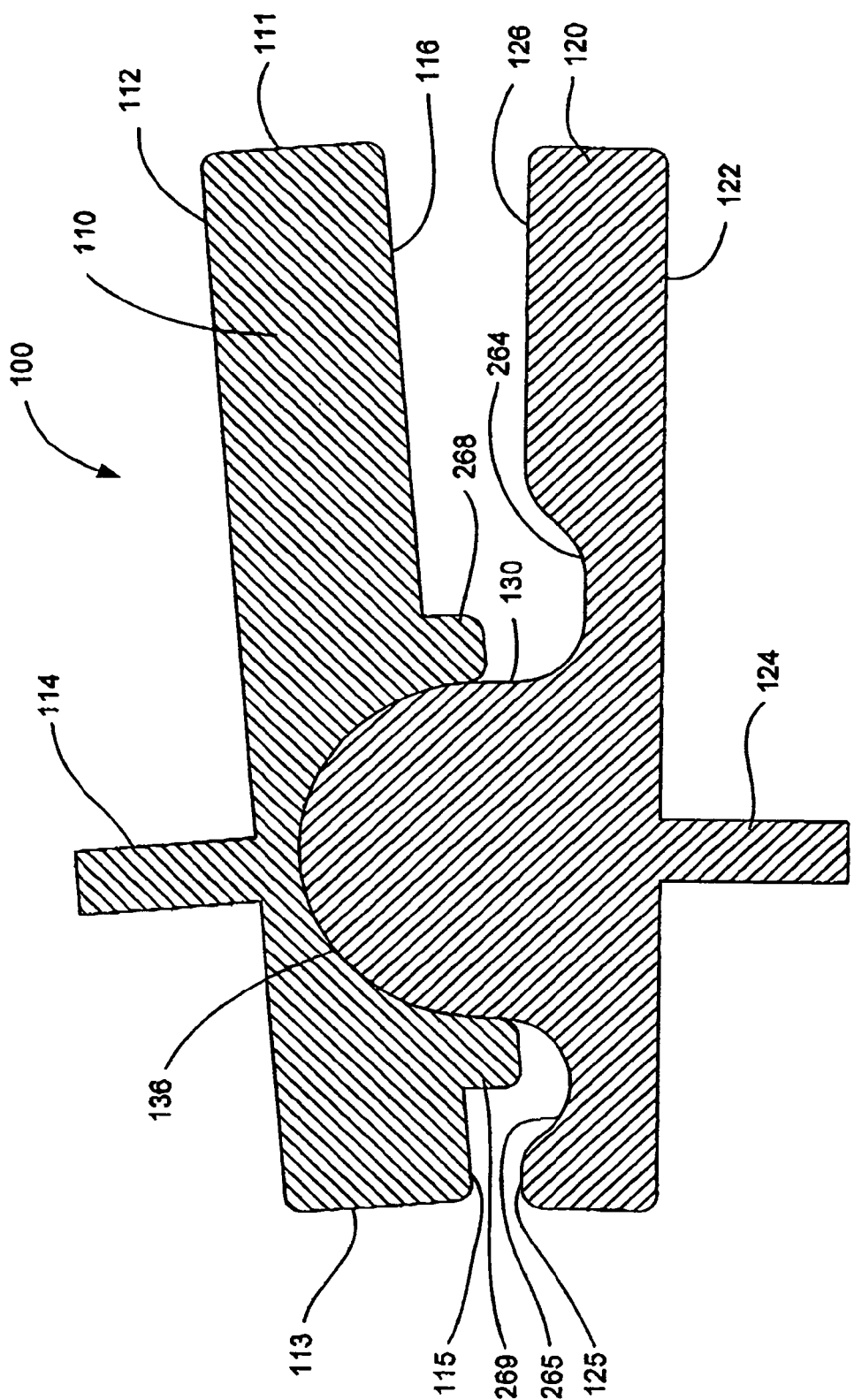
FIG. 2D is a partial cross-sectional view of an alternative embodiment of the implant of the invention having a protuberance adjacent the socket.

FIG. 2C and FIG. 2D show cross sections of implant 100 through the sagittal plane of the vertebrae. FIG. 2C is a cross-section of the side view of the intervertebral implant 100 showing the mating of the spacer 130 to the socket 136. FIG. 2D illustrates an alternate embodiment of the first end plate 110 wherein the socket 136 has ridges 268, 269 forming a protuberance that extends into the channel 264, 265 respectively on the second end plate 120. As will be appreciated by those of skill in the art, the protuberances 268, 269 can extend partially into the channel, such as the configuration shown, or can have a channel conforming shape such that when the spacer and socket are moved to achieve flexion 272 or extension 274 the protuberance or ridge 268, 269 extends into the channels 264, 265. This embodiment allows the first inner surface 116 and second inner surface 126 of the first end plate 110 and the second end plate 120 to be flat and non-sloping as shown while still allowing for the implant to emulate forward and backward bending and allow for the blocking of the motion of the socket relative to the spacer. In this embodiment, it is noted that the first and second keels 114,124 are aligned with and support the articulation of first end plate 110 about the spacer 130 for this embodiment, and where the articulation is about perpendicular to the sagittal plane of the spine.

Figure 3A:
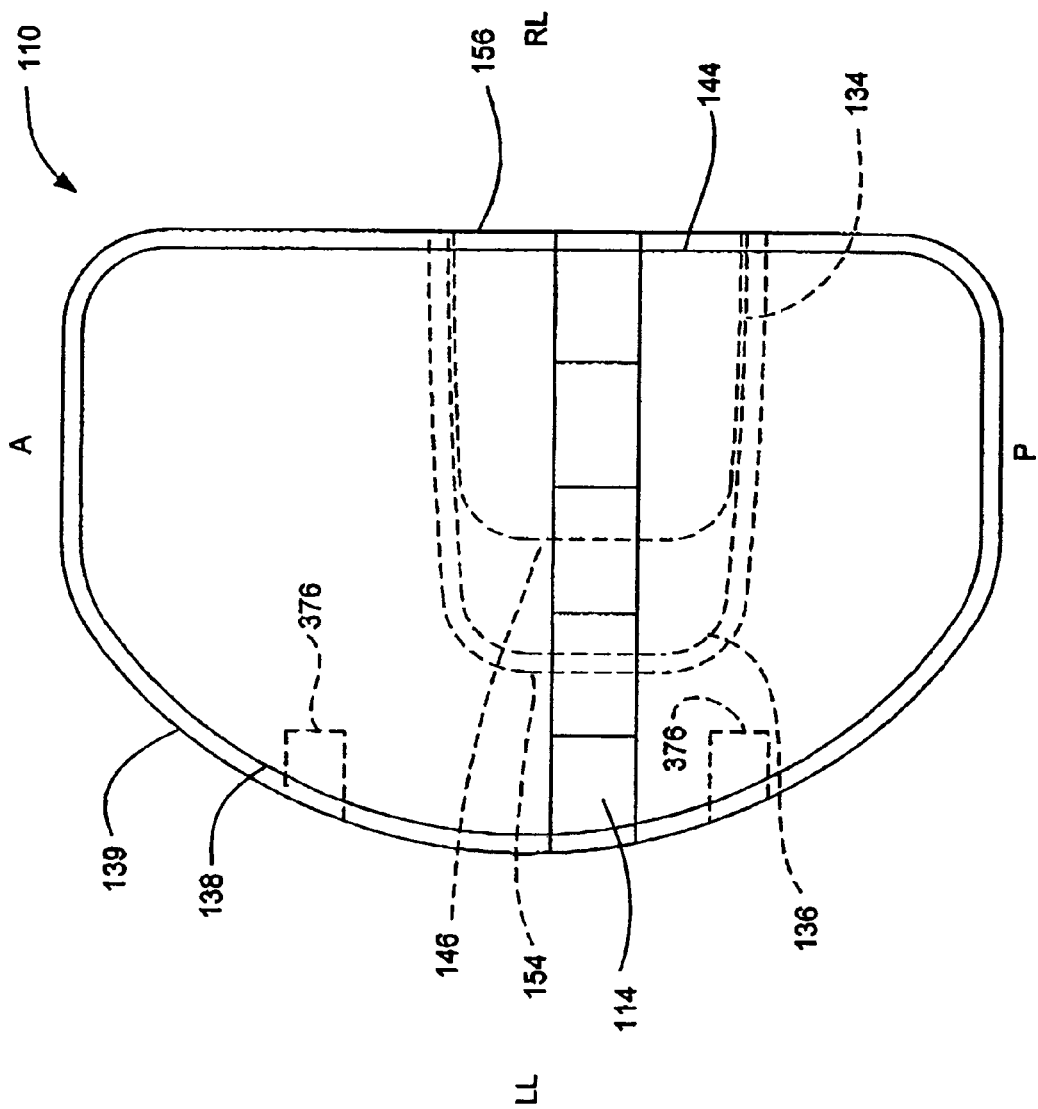
FIG. 3A is a top view of a portion of an embodiment of the assembled implant of the invention.
Figure 3B:
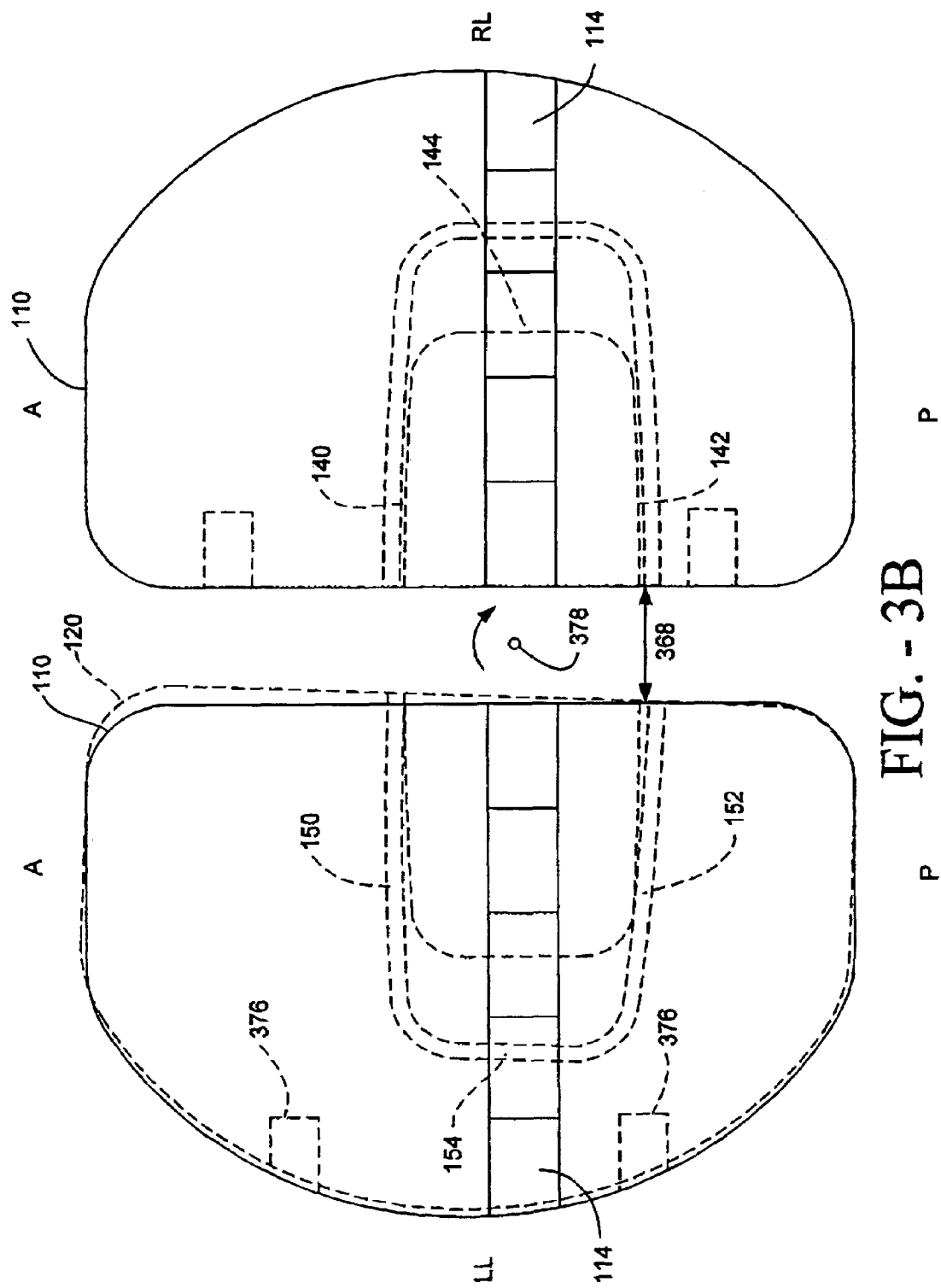
FIG. 3B is a top view of an embodiment of the implant of the invention showing a rotation to the right.
Figure 3C:
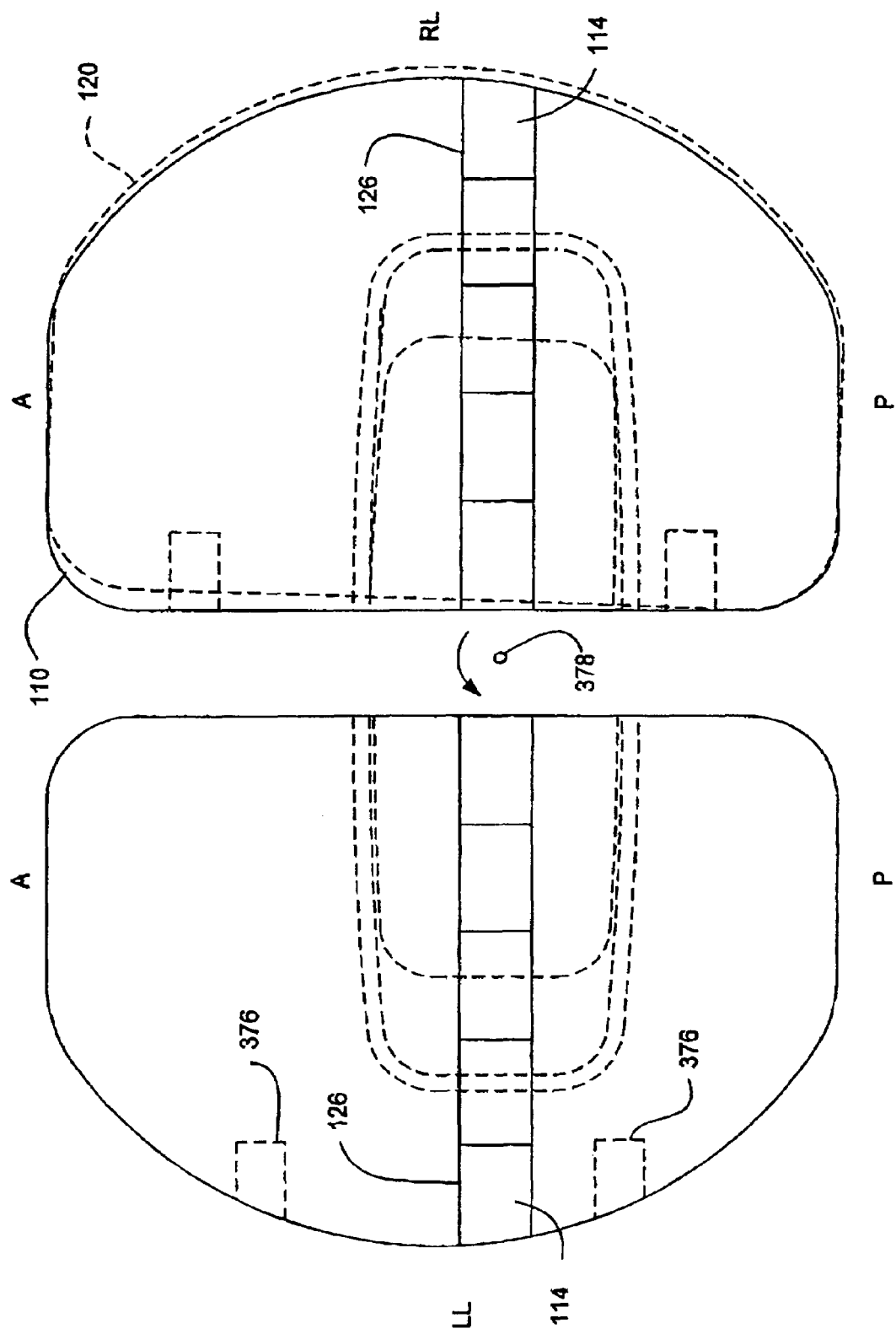
FIG. 3C is a top view of an embodiment of the implant of the invention showing a rotation to the left.

Turning now to FIG. 3A, a top view of one-half of the intervertebral implant 100 is shown. Each of the top first end plate 110 and the bottom second end plate 120 have a bores 376 for receiving pins of an implant tool. The first keel 114 on the first end plate 110 is positioned so that it is aligned in the same plane with the second keel 124 on the second end plate 120. Additionally, the length of spacer 130 from the third end wall 144 to the fourth end wall 146 is shorter than the length of the socket 136 from the end wall 154 to the open end 156, so that the fit of the spacer with the socket is somewhat loose. The loose fit of the spacer 130 in the socket 136 allows the first end plate 110 to be able to twist somewhat relative to the second plate 120. This twisting action would generally be about an axis that is perpendicular to the first and second inner surfaces 116,126 of the first and second end plates 110,120, respectively. Thus, implant 100 of this embodiment allows the spine to have movement in three orthogonal degrees of freedom, namely (1) forward and backward bending movement, (2) lateral side-to-side bending, and (3) twisting movement. FIGS. 3B and 3C show the relative rotation of the first or upper end plate 110 to the second or lower end plate 120 to achieve rotation about a central axis 378. This rotation results in about a 3°-6° rotation about the axis (i.e., 3° of torso twisting in each direction).

Figure 4A:
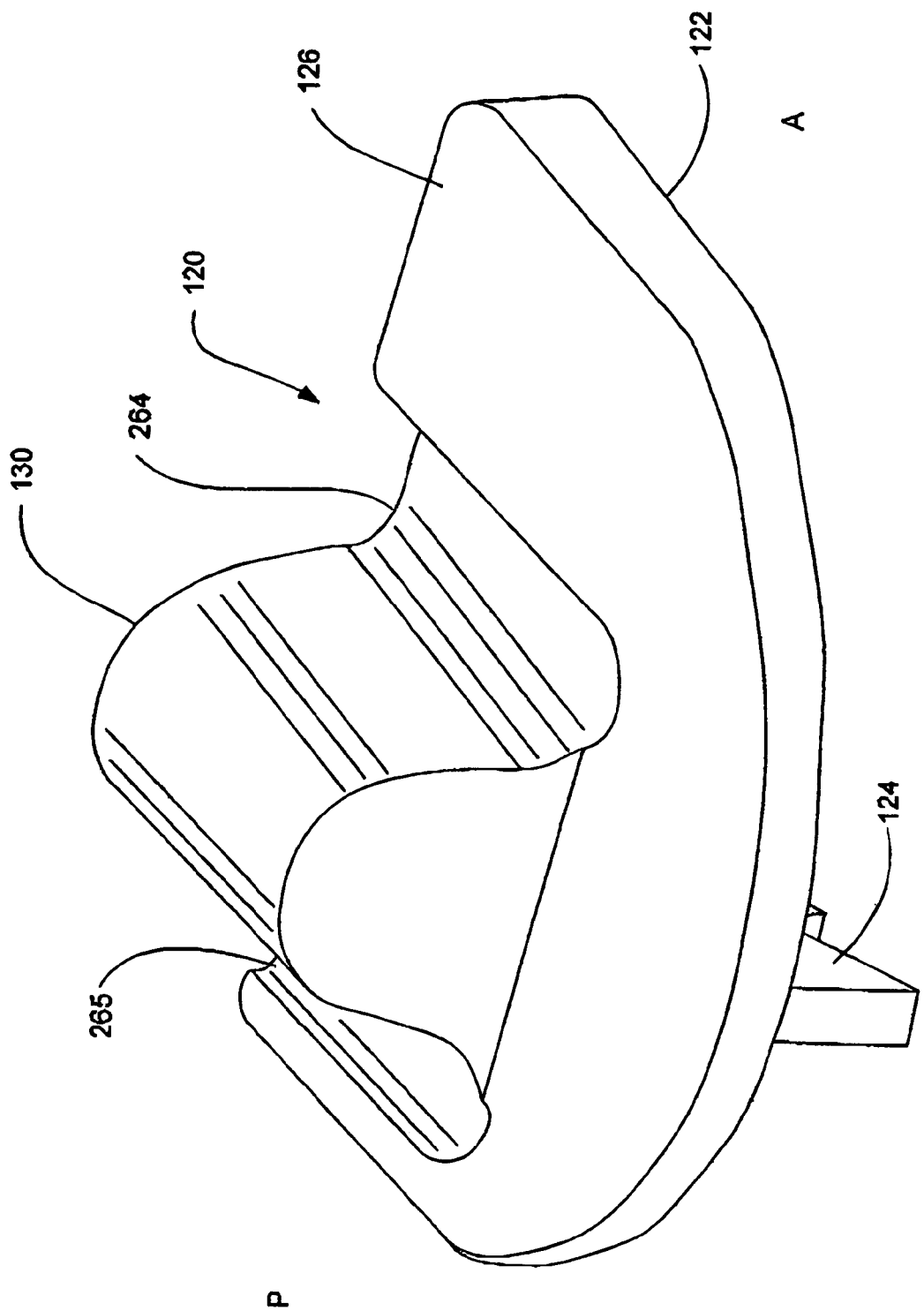
FIG. 4A and FIG. 4B show perspective views of the first and second inner surfaces of the first end plate and the second end plate of an embodiment of implant 100.
Figure 4B:
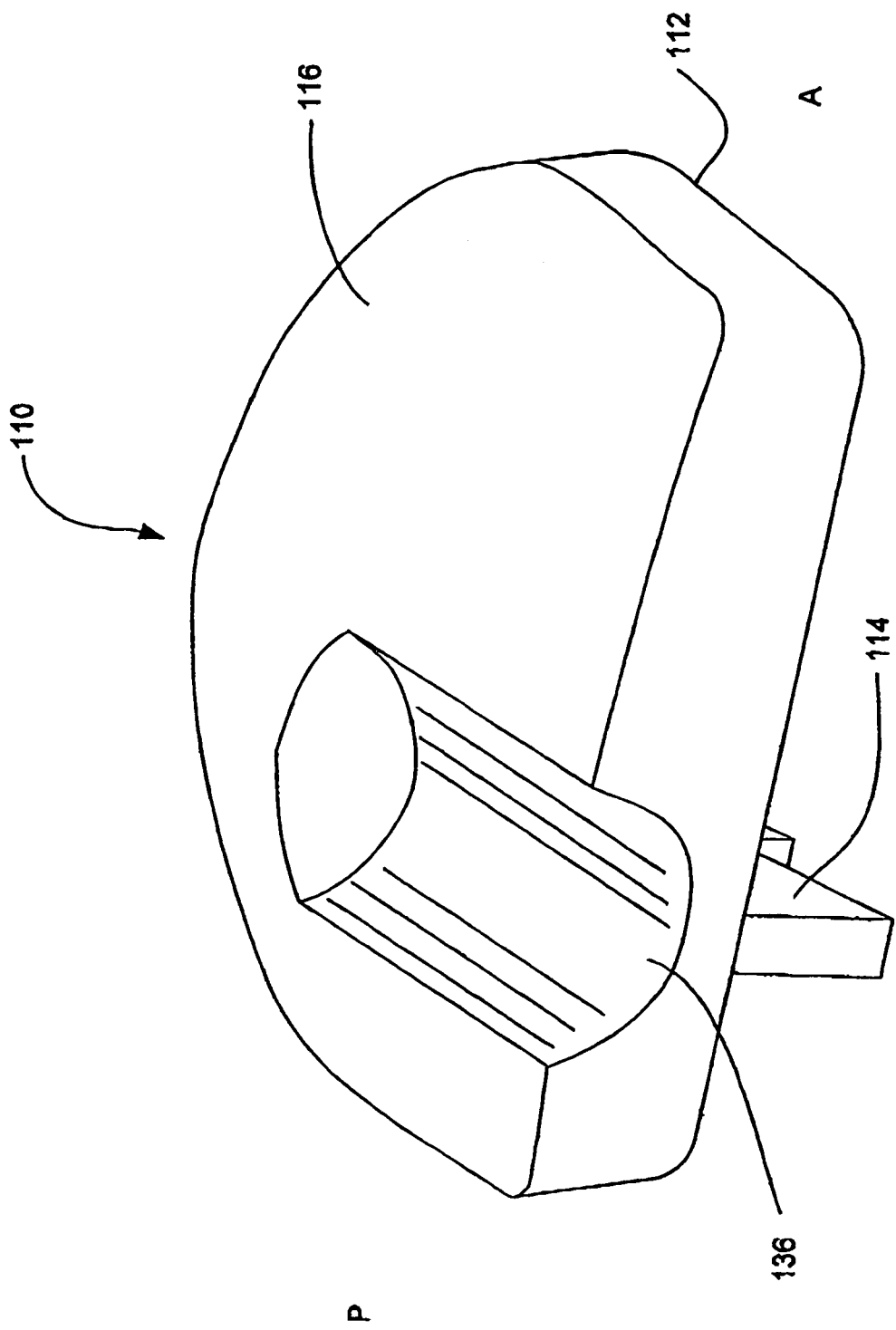

FIG. 4A and FIG. 4B show views of the first and second end plates, 110, 120. FIG. 4A shows a perspective view of a second end plate 120 of the intervertebral implant 100. The second inner surface 126 of the second end plate 120 is shown with a hemi-cylindrical spacer 130 formed therefrom, and channels or grooves 264, 265 extending about the spacer 130. As illustrated in FIG. 4A, the channels 264, 265 are formed on two sides of the spacer 130. However, as will be appreciated by those of skill in the art, the channels 264, 265 can alternatively surround the spacer 130. The channels allow the sides of the spacer 130 to be made more perpendicular so as to create a greater blocking wall thus preventing the socket of the upper plate 100 from moving too much anteriorly or posteriorly relative to the lower plate 120. FIG. 4B shows a perspective view of the first end plate 110, with a first inner surface 116 that opposes the second inner surface 126. The first inner surface 116 has a hemi-cylindrical socket 136 formed therein. The socket 136 of FIG. 4B is configured to mate with the spacer 130 of FIG. 4A.

FIG. 4C and FIG. 4D show views of the first and second end plates, 110, 120 for an alternative embodiment of implant 100. FIG. 4C shows a perspective view of an embodiment of the second inner surface 126 of the second or lower end plate 120 of implant 100. The second inner surface 126 of the lower end plate 120 has a hemispherical spacer 130 formed therefrom. FIG. 4d shows a perspective view of an embodiment of the first inner surface 116 of the first or upper end plate 110 of implant 100, which opposes the second inner surface 126. The first inner surface 116 of the upper end plate 110 has a socket or cavity 136 formed therein. In the embodiment of FIG. 4d, the socket 136 has a concave hemispherical surface. The socket 136 allows the first end plate 110 to pivot or rotate on spacer 130.

In the embodiments shown in FIG. 4A and FIG. 4B, it is noted that the first and second keels 114,124 are aligned with and support the articulation of the first end plate 110 about the spacer 130, relative to the second end plate 120. The first and second keels 114,124 in this orientation offer substantial stability during extension and flexion for implant 100 inserted between the vertebrae of a patient. Additionally, the first and second keels 114,124 in these embodiments are aligned with and support the lateral axis of articulation of implant 100, which is perpendicular to the sagittal plane of the spine. Additionally, as evidenced from the perspective views of FIG. 4A and FIG. 4B, the perimeter shape of the upper and lower end plates 110,120 can be configured to correspond to the perimeter shape of a vertebral disk. As will be appreciated by those of ordinary skill in the art, the perimeter shape of the upper end plate 110 and the lower end plate 120 can be the same.

Figure 5A:
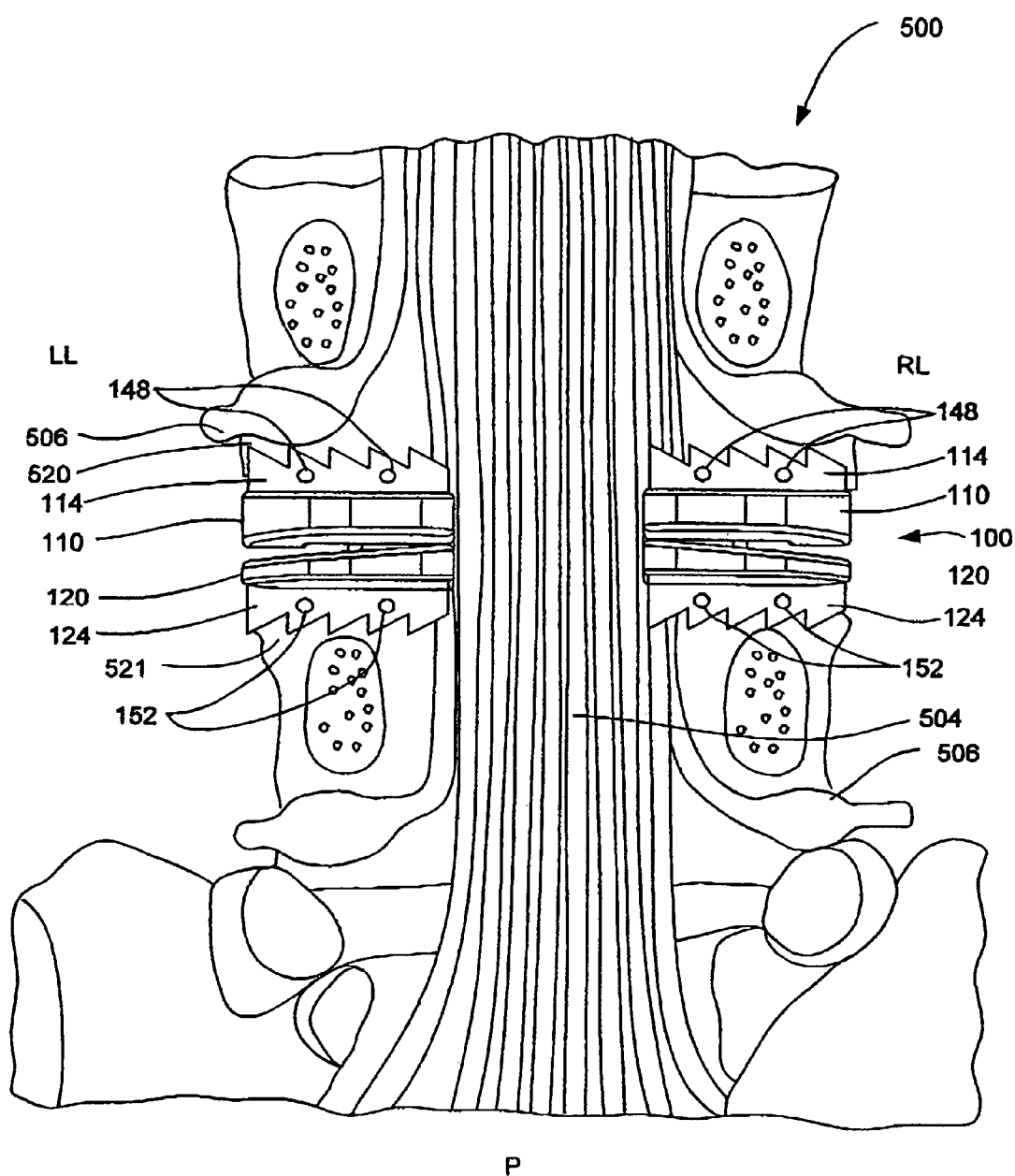
FIG. 5A is a posterior view of the embodiment of the implant of the invention after being implanted between two vertebral bodies.
Figure 5B:
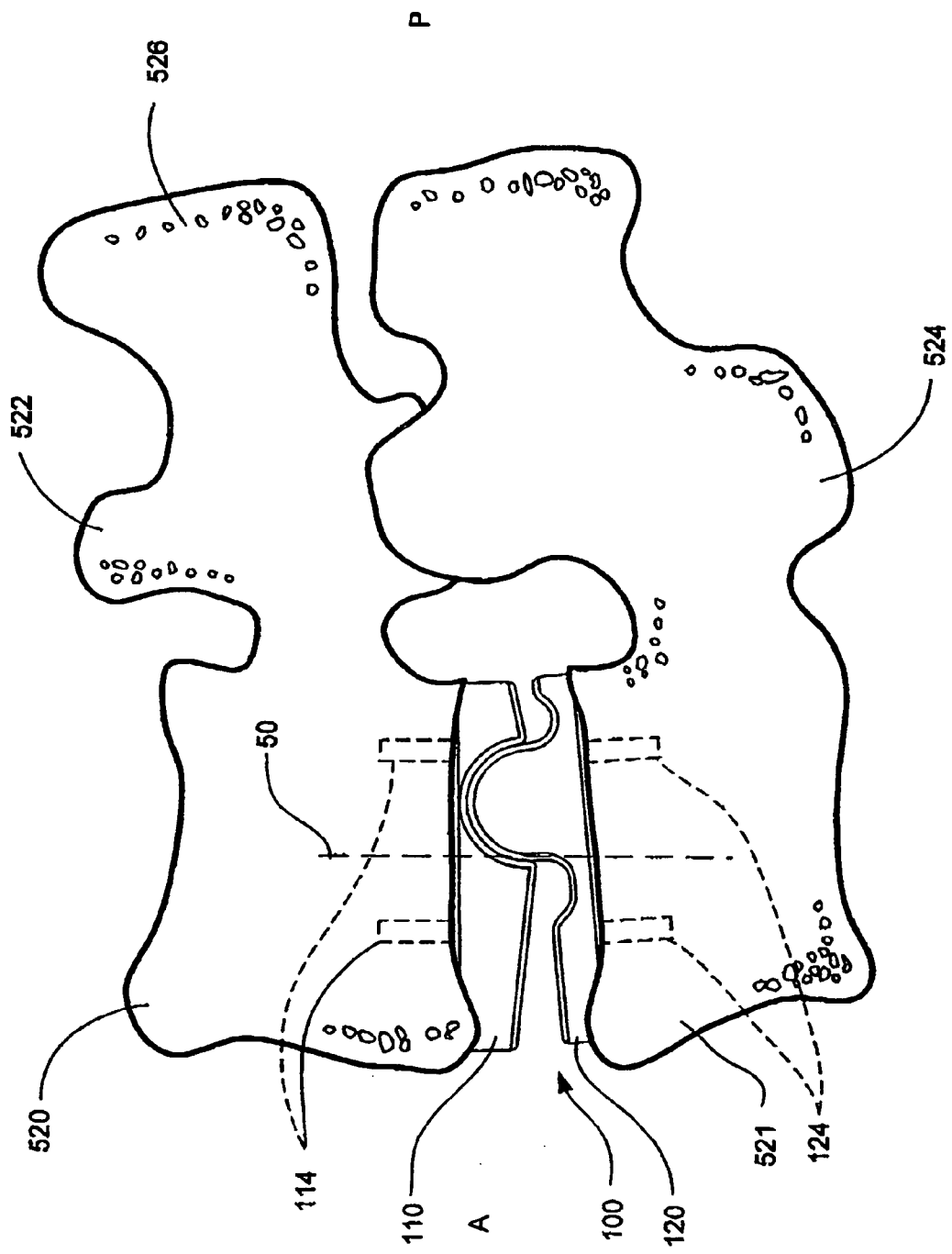
FIG. 5B is a side view of the embodiment of the implant of the invention after being implanted between two vertebral bodies.

FIG. 5A and FIG. 5B show the implant after insertion between the vertebrae of a patient. FIG. 5A illustrates a posterior view of the implant shown in FIG. 1A implanted between vertebral bodies in a spine. FIG. 5A illustrates the spinal column 500 and the cauda equina 504 (a collection of lumbar and sacral nerve roots that fill the caudal end of the spinal cord) with individual nerves 506 exiting the cord between lumbar vertebrae. The implant 100 is positioned between two vertebral bodies 520, 521 such that the first and second keels 114, 124 lie in a plane parallel to coronal or frontal plane of the body, or perpendicular to the sagittal plane of the vertebrae. FIG. 5B illustrates a side view of the implant inserted between vertebral bodies 520, 521, for embodiments of the implant as that shown in FIG. 1A, or FIG. 6A. The gap between the first end plate 110 and the second end plate 120 at the anterior "A" face of implants 100,600 is greater than at the posterior "P" face of implants 100,600. The greater gap at the anterior face vs. the posterior face of implants 100, 600 results in the flexion (forward bending) movement being facilitated to a greater degree than extension (backward bending) movement. Thus, for these embodiments, an example of a forward bending movement of up to 10° can be achieved while a backward bending movement of 5° will be achieved. These embodiments show implants 100,600 inserted between two vertebrae with two first keels 114 extending from the first end plate 110, and two second keels 124 extending from the second end plate 120. The first and second keels 114,124 are about perpendicular to the sagittal plane of the spine, and support the articulation of the first end plate 110 relative to the second end plate 120, about the spacer 130.

The embodiments of implants 100, 600 can be made of medical grade titanium, stainless steel or cobalt chrome. Other materials that have appropriate structural strength and that are suitable for implantation into a patient can also be used.

One class of materials contemplated for use in implant 100 is the class of biocompatible polymers. Copolymers, blends and composites of polymers are also contemplated for fabrication of parts of the disclosed device. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer.

One group of biocompatible polymers are the polyaryl ester ketones which has several members, which include polyetheretherketone (PEEK), and polyetherketoneketone (PEKK). PEEK has proven as a durable material for implants, as well as meeting criteria of biocompatibility. Medical grade PEEK is available from Victrex Corporation under the product name PEEK-OPTIMA. Medical grade PEKK is available from Oxford Performance Materials under the name OXPEKK, and also from CoorsTek under the name Bio-PEKK. Still another interesting group of biocompatible polymers are polyalkyl biocompatible polymers, such as polyethylenes, polypropylenes, and the like.

These medical grade biocompatible polymers are also available as reinforced polymer materials. To reinforce a polymeric material, fillers, are added to a polymer, copolymer, polymer blend, or polymer composite. Fillers are added to modify properties, such as mechanical, optical, and thermal properties. In this case, fillers, such as carbon fibers, are added to reinforce the polymers mechanically to enhance strength for certain uses, such as load bearing devices.

In addition to disclosure of embodiments of an intervertebral implant, tools for preparing and inserting an intervertebral implant are also disclosed. FIG. 7A through 7D show an embodiment of a tool for preparing vertebral bodies to receive implants 100,600, while FIG. 8A through FIG. 8D show an embodiment of a tool for inserting embodiments of the disclosed intervertebral implants 100,600.

Figure 7A:
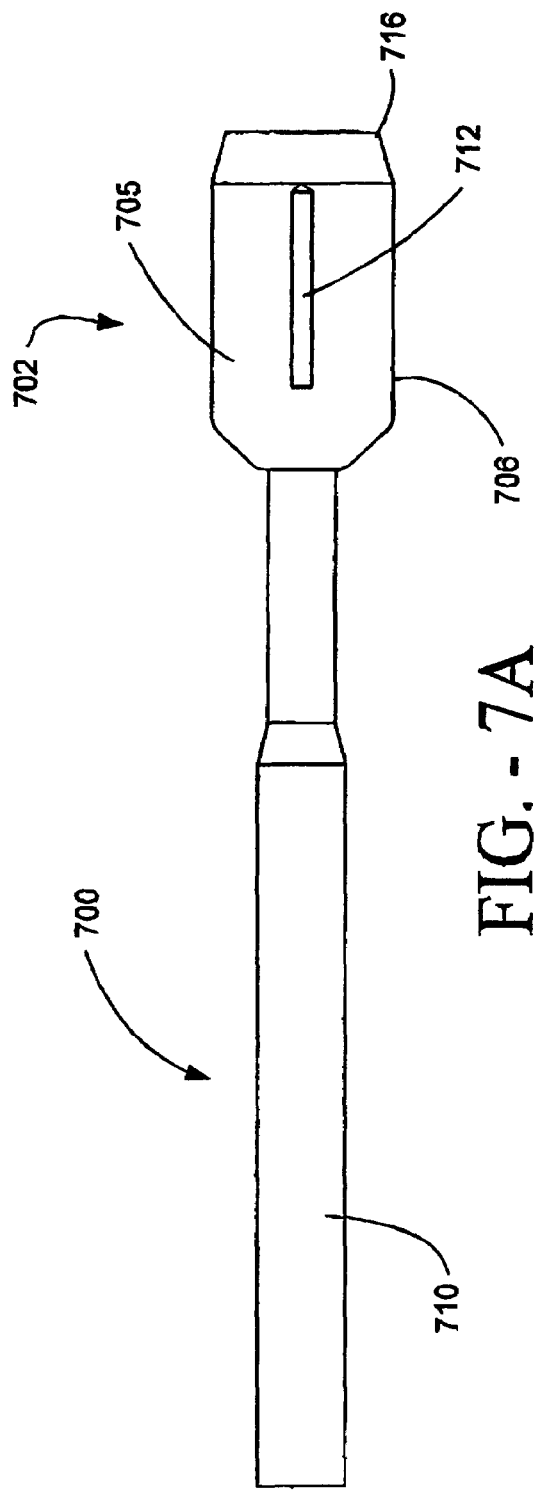
FIG. 7A is a top view of an embodiment of a cutting tool of the invention used to prepare the vertebral bodies for the implant.
Figure 7B:
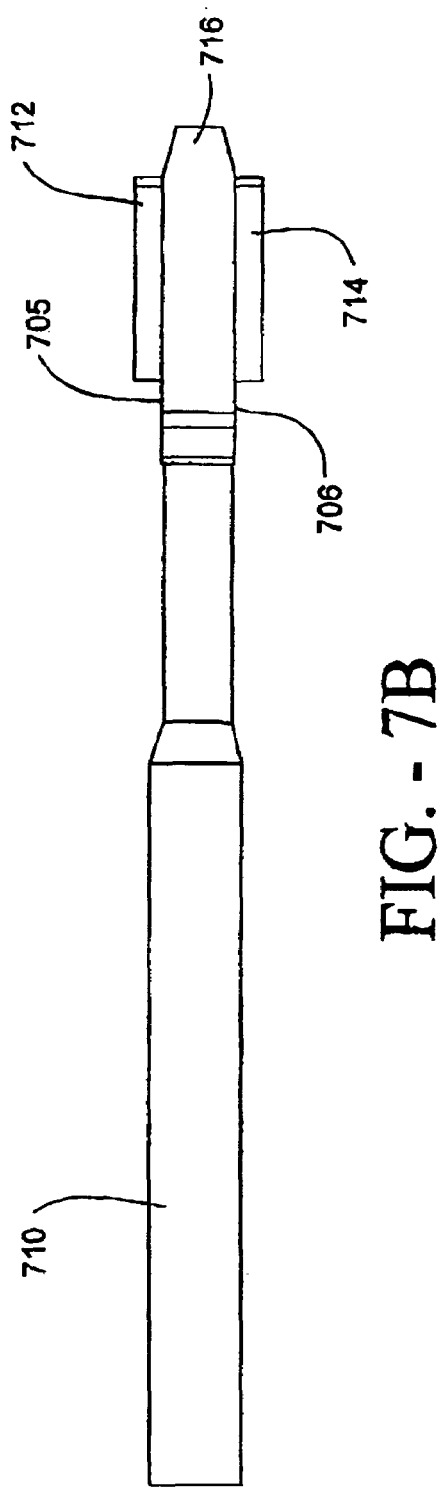
FIG. 7B is a side view of the embodiment of the cutting tool of the invention from the distal end.
Figure 7C:
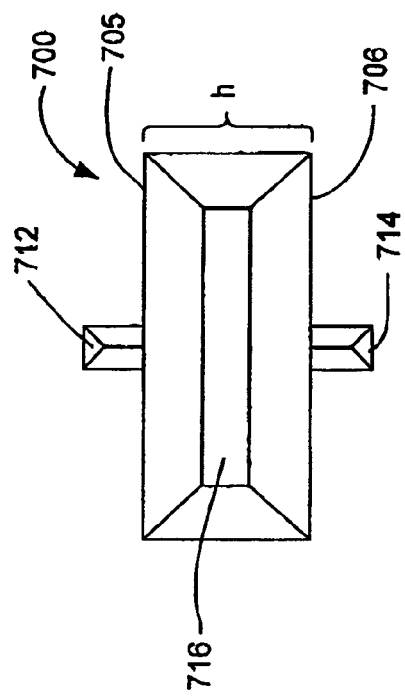
FIG. 7C is a distal end view of an embodiment of the cutting tool of the invention.
Figure 8D:
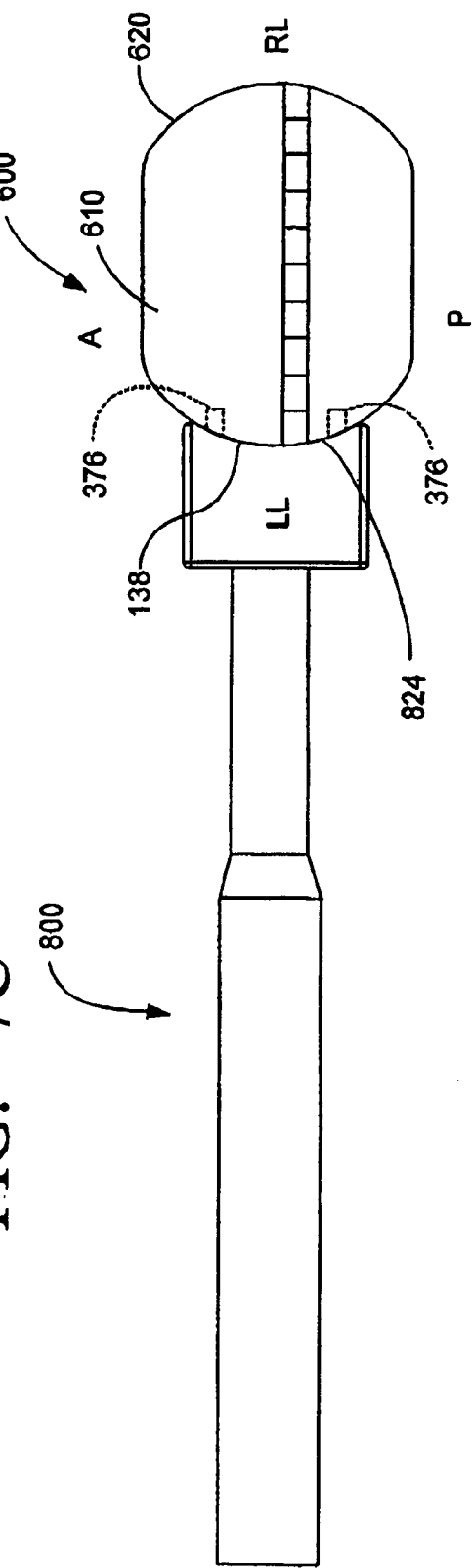
FIG. 8D is a top view of an embodiment of the implant lateral insertion tool holding an embodiment of the implant.

FIG. 7A through FIG. 7C are the top view, the side view, and an end view of the cutting tool 700. The cutting tool 700 has a handle 710 at its proximal end for controlling the tool during operation. As will be appreciated by those of skill in the art, the handle 710 can be removable or affixed to the cutting end. The distal end 702 of the tool 700 is solid head has an upper surface 705, and a lower surface 706. The upper surface 705 has a first blade 712 mounted thereon, and the lower surface 706 has a second blade 714 mounted thereon. Preferably the first blade 712 is about centered with the upper surface 705, and the second blade 714 is about centered with the lower surface 706. The first and second blades 712,714 are oriented to cut a space in a first and second intervertebral body for the first and second keels 114,124 of implants 100,600. The space is perpendicular to the sagittal plane of the vertebrae, and allows for the lateral insertion of the implants 100, 600. FIG. 7C is a view of the distal end of the cutting tool 700 showing the beveled end 716 and the first and second blades 712,714. The height h of the head 702 of the cutting tool 700 approximates the distance between two vertebral bodies or the height of the disk space. In this embodiment of cutting tool 700, the blades 712, 714 extend above and below the head 702.

As will be appreciated by those of skill in the art, the tool shown in FIG. 7A can be modified such that instead of cutting keel-receiving channels in the upper and lower vertebral bodies at the same time, two tools are provided so that only one vertebral body is cut for keel-receiving channels at a time. For example, an alternative embodiment of cutting tool 700 has a first tool with a single blade mounted on the head 702. A second tool could be provided having a single blade mounted on the head 702, and additionally on the opposing surface, a guide. The guide on the surface opposite the surface with the blade is designed to engage with the first keel receiving channel cut the first vertebrae with the first tool to ensure that the second cut is optimally aligned with the first cut.

Figure 8C:
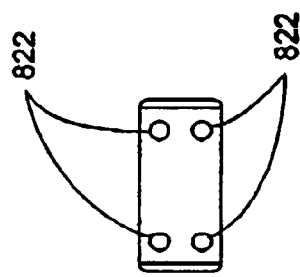
FIG. 8C is a distal end view of the embodiment of the implant lateral insertion tool of the invention.

FIG. 8A through FIG. 8D depict an embodiment of the implanting tool used to insert the implant 600 of FIG. 6A between vertebral bodies. FIG. 8A is a side view of the implantation tool 800 that has a handle 810 and an implant holder 820. The implant holder 820 has an implant conforming surface 824 and four pins 822 for holding the first end plate 610 and the second end plate 620 implant 600. The conforming surface 824 is curved to follow the convex outer LL edges of the first and second end plates 610, 620, respectively, for an implant inserted from the left lateral side of a patient. The implant 600 nests within a conforming surface 824 and is held by pins 822. FIG. 8C shows the distal view of the end of the tool with four pins 822 for securing the first and second end plate of the implant.

A variety of kits can be assembled that include an implant 100 (or 600) sized for a particular patient. The kit could also include several cutting tools 700 and several implanting tools 800 or a single handle that cooperates with cutting ends 702 and implantation ends 820.

Figure 9:
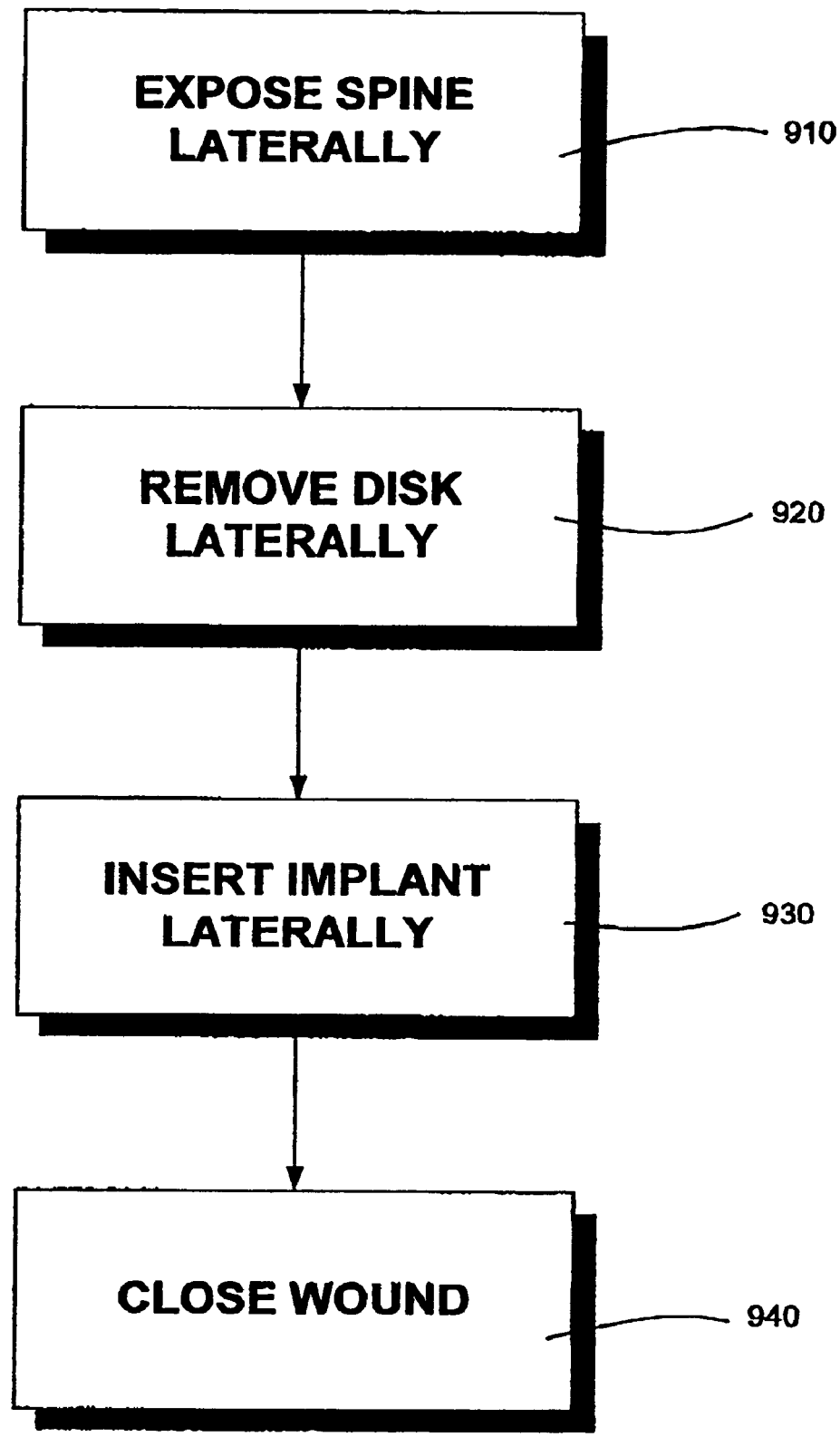
FIG. 9 is a block diagram illustrating the steps of a method for inserting the implant between vertebral bodies.

FIG. 9 is a block diagram showing the basic steps of the method for laterally inserting the embodiments of implants 100,600. First the spine is exposed through a lateral access 910, then the intervertebral disk is removed laterally 920, if necessary. A tool, such as the one depicted in FIG. 7A is inserted laterally between the vertebral bodies to create channels in the bodies to receive the keels of the implant. The implant is then inserted laterally 930 between two vertebrae and the wound is closed 940. This procedure can be followed for either a left lateral approach or right lateral approach. For a left lateral approach, the teeth 115,125 of upper and lower keels 114, 124 would be pointed towards the left lateral face of the device in order to aid in retaining embodiments of implants 100,600 in place. For a right lateral approach, the teeth would point towards the right lateral face of the device.

What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the embodiments described herein, thereby enabling others skilled in the art to understand the various embodiments and various modifications that are suited to the particular use contemplated. It is intended that the scope of what is disclosed be defined by the following claims and their equivalence.

What is claimed:

1. A method of inserting an intervertebral implant between adjacent vertebral bodies of a spine, comprising:
   accessing a lateral side of an intervertebral space;
   preparing the intervertebral space for insertion of the intervertebral implant; and
   inserting the intervertebral implant laterally into the intervertebral space, the intervertebral implant comprising a pair of implants adapted to be positioned a lateral distance apart from each other when inserted between the adjacent vertebral bodies, the intervertebral implant having a translating pivot point and laterally extending attachment mechanisms adapted to extend along a lateral direction with respect to the vertebral bodies when inserted therebetween,
   wherein inserting the intervertebral implant includes:
      inserting the laterally extending attachment mechanism on a first implant of the pair of implants between the adjacent vertebral bodies, and
      inserting the laterally extending attachment mechanism on a second implant of the pair of implants between the adjacent vertebral bodies along the same insertion path as the laterally extending attachment mechanism of the first implant of the pair implants.

2. The method of claim 1 further comprising removing an affected disk before preparing the intervertebral space for insertion of the implant.

3. The method of claim 1 wherein each pair of implants further comprises:
   a socket having an elongated curved inner surface; and
   a spacer having an elongated curved top surface adapted to be in contact with the curved inner surface of the socket.

4. The method of claim 1 wherein the attachment mechanisms are aligned with and support the implant.

5. The method of claim 1 wherein the translating pivot point accommodates a bending movement and twisting movement of the spine.

6. The method of claim 1, wherein inserting the intervertebral implant laterally comprises:
   inserting the first implant of the pair of implants into the prepared intervertebral space from a lateral side; and inserting the second implant of the pair of implants into the prepared intervertebral space from the same lateral side as the first implant of the pair of implants.

7. A method of inserting an intervertebral implant between upper and a lower vertebral bodies, comprising:
    accessing a lateral side of an intervertebral space;
    cutting a lateral keel receiving channel into a vertebral body; where the lateral keel receiving channel is substantially perpendicular to the sagittal plane of the vertebral body; and
    inserting an intervertebral implant between the upper and lower vertebral bodies, wherein the intervertebral implant comprises first and second implant portions adapted to be positioned a distance apart from each other when inserted between the upper and lower vertebral bodies, each of the first and second implant portions further comprises:
        a first end plate adapted to mate with the upper vertebral body, further comprising:
            a first inner surface having a socket therein;
            a first outer surface; and
            at least one laterally oriented keel on the first outer surface adapted to be inserted into the keel receiving channel;
        a second end plate adapted to mate with the lower vertebral body further comprising:
            a second inner surface opposing the first inner surface, wherein the second inner surface has a spacer formed thereon configured to fit within the socket;
            a second outer surface; and
            wherein the spacer and socket provide a translating pivot point positioned between the first end plate and the second end plate,
    wherein inserting an intervertebral implant includes:
        inserting the laterally oriented keel on the first outer surface of the first implant portion into the keel receiving channel, and
        inserting the laterally oriented keel on the first outer surface of the second implant portion into the same keel receiving channel.

8. The method of claim 7 further comprising removing an affected disk before cutting a lateral keel receiving channel into the vertebral body.

9. The method of claim 7 wherein inserting an intervertebral implant further comprises pushing the implant between the upper and lower vertebral bodies utilizing a implantation tool.

10. The method of claim 7 wherein cutting the lateral keel receiving channel further comprises cutting the keel receiving channel utilizing a keel cutting tool.

11. The method of claim 7 wherein the keel on the first outer surface is aligned with and supports the spacer.

12. The method of claim 7 wherein the second outer surface further comprises a second keel extending therefrom.

13. The method of claim 12 wherein the second keel on the second outer surface is aligned with and supports the spacer.

14. The method of claim 7 wherein the translating pivot point accommodates a bending movement and a twisting movement of the spine.

15. A method of inserting an intervertebral implant between adjacent upper and a lower vertebral bodies, comprising:
    accessing a lateral side of an intervertebral space;
    cutting a keel receiving channel into a vertebral body utilizing a keel cutting tool, wherein the keel receiving channel is oriented between lateral sides of the vertebral bodies; and
    inserting a portion of an intervertebral implant into the keel receiving channel utilizing an implantation tool, wherein the intervertebral implant comprises a pair of implants adapted to be positioned a lateral distance apart from each other when inserted between the upper and lower vertebral bodies, wherein each pair of implants includes a spacer having a translating pivot point,
    wherein inserting a portion of an intervertebral implant includes:
        inserting a laterally oriented keel of a first implant of the pair of implants into the keel receiving channel, and
        inserting a laterally oriented keel of a second implant of the pair of implants into the same keel receiving channel.

16. The method of claim 15 further comprising removing an affected disk before cutting a lateral keel receiving channel into the vertebral body.

17. The method of claim 15 wherein the keel of the first implant of the pair of implants is oriented to be perpendicular to the sagittal plane of the spine when inserted therein.

18. The method of claim 17 wherein the keel on the second implant of the pair of implants is aligned with and supports the spacer.

19. The method of claim 15 wherein the translating pivot point accommodates a bending movement and a twisting movement of the spine.

20. The method of claim 15 wherein the translating pivot point further comprises:
    a first end plate of the implant including a socket therein; and
    a second end plate of the implant including an elongated spacer extending therefrom, wherein the elongated spacer fits within the socket.

21. A method of implanting an intervertebral implant between adjacent vertebral bodies in a spine comprising:
    cutting keel receiving channels in adjacent vertebral bodies utilizing a keel cutting tool, wherein the keel receiving channels are oriented between a first lateral side and a second lateral side of the vertebral bodies; and
    inserting an intervertebral implant into the keel receiving channels, wherein the intervertebral implant comprises a pair of implants adapted to be positioned a lateral distance apart from each other when inserted between the adjacent vertebral bodies,
    wherein inserting an intervertebral implant into the keel receiving channels includes:
        inserting a laterally oriented keel of a first implant of the pair of implants into one of the keel receiving channels, and
        inserting a laterally oriented keel of a second implant of the pair of implants into the same one of the keel receiving channels.

22. A method of implanting an intervertebral implant between adjacent vertebral bodies in a spine comprising:
    pushing an intervertebral implant comprising a pair of implants adapted to be positioned a lateral distance apart from each other when inserted between the adjacent vertebral bodies having a plurality of keels into corresponding keel receiving channels in adjacent vertebral bodies utilizing an implantation tool, wherein the intervertebral implant is pushed between the adjacent vertebral bodies from a lateral approach, wherein pushing an intervertebral implant includes:
sequentially inserting a laterally oriented keel of a first implant of the pair of implants into one of the keel receiving channels with the implantation tool, and
inserting a laterally oriented keel of a second implant of the pair of implants into the same one of the keel receiving channels.

* * * * *